United States Patent [19]
Cimochowski et al.

[11] Patent Number: 5,967,989
[45] Date of Patent: Oct. 19, 1999

[54] ULTRASONIC SENSORS FOR MONITORING THE CONDITION OF A VASCULAR GRAFT

[75] Inventors: George E. Cimochowski, Dallas, Pa.; George W. Keilman, Woodinville, Wash.

[73] Assignee: VascuSense, Inc., Woodinville, Wash.

[21] Appl. No.: 09/079,818

[22] Filed: May 15, 1998

Related U.S. Application Data

[62] Division of application No. 08/949,413, Oct. 14, 1997, Pat. No. 5,807,258.

[51] Int. Cl.$^6$ ........................................................ A61B 8/00
[52] U.S. Cl. ........................... 600/459; 600/462; 128/903
[58] Field of Search ................................. 600/454, 459, 600/494, 473, 500, 504, 455, 505, 317

[56] References Cited

U.S. PATENT DOCUMENTS

| | | | |
|---|---|---|---|
| 4,198,987 | 4/1980 | Cain et al. | 128/663 |
| 4,227,407 | 10/1980 | Drost | 73/194 A |
| 4,550,606 | 11/1985 | Drost | 73/626 |
| 4,926,875 | 5/1990 | Rabinovitz et al. | 128/691 |
| 5,205,292 | 4/1993 | Czar et al. | 128/662.03 |
| 5,289,821 | 3/1994 | Swartz | 128/661.09 |
| 5,368,039 | 11/1994 | Moses | 600/494 |
| 5,411,551 | 5/1995 | Winston et al. | 623/1 |
| 5,453,576 | 9/1995 | Krivitski | 128/668 |
| 5,588,436 | 12/1996 | Narayanan et al. | 128/662.03 |
| 5,595,182 | 1/1997 | Krivitski | 128/692 |
| 5,628,782 | 5/1997 | Myers et al. | 623/1 |
| 5,669,388 | 9/1997 | Vilkomerson | 600/455 |
| 5,680,863 | 10/1997 | Hossack et al. | 600/459 |
| 5,833,603 | 11/1998 | Kovacs et al. | 600/317 |

FOREIGN PATENT DOCUMENTS

| | | | |
|---|---|---|---|
| WO98/08466 | 5/1998 | WIPO | A61F 2/06 |

OTHER PUBLICATIONS

Vilkomerson, David, et al., "Higher–Order Diffracting–Grating Transducers," SPIE, vol. 3037,0277–786X/97, pp. 206–212.

"Cardiac Output," Medical Electronics, Apr. 1996, 7 pp.

Crystal Biotech, Inc. Brochure, "2/4/T Transducer System," CBI Physiological Research Systems CBI–8000, 2 pp.

Crystal Biotech, Inc. (CBI) Brochure, "Blood Flow Transducers, DBF Soft Silastic®, Assemblies and Transducers for Pulsed Doppler Blood Flow Velocimetry," Data Sciences International, 2 pp.

Crystal Biotech, Inc. (CBI) Brochure, "Blood Flow Transducers, HDP Hard Epoxy Transducers for Pulsed Doppler Flow Velocimetry," Data Sciences International, 2 pp.

(List continued on next page.)

*Primary Examiner*—Francis J. Jaworski
*Assistant Examiner*—Ali M. Imam
*Attorney, Agent, or Firm*—Ronald M. Anderson

[57] ABSTRACT

A parameter indicative of the status of fluid flow is remotely monitored in a vessel, a natural graft, or a synthetic graft. One or more transducers are provided either in a wall of a synthetic graft or adjacent to a vessel or natural graft to monitor the parameter. A conformal array transducer or a tilted element is used to monitor fluid flow or velocity through the graft or vessel based on the effect of the fluid on ultrasonic waves produced by the transducers. The conformal array transducer comprises a plurality of elements that curve around the graft or vessel and are excited with an input signal provided by an implantable electronics circuit, producing ultrasonic waves that propagate into the fluid flowing within the graft or vessel. Transit time or Doppler measurements are made using an appropriate number of these transducer to determine either fluid flow or velocity. Various implantable electronic circuits are provided that enable a selected transducer to be driven and to receive an ultrasonic signal or a pressure signal indicative of the status of fluid flow monitored by the transducer. The implanted electronic circuit is connected to an implanted radio frequency (RF) coil. An external coil that is connected to a power supply and monitoring console is coupled to the implanted RF coil to convey power and receive data signals from the transducer that are indicative of the parameter being monitored.

18 Claims, 10 Drawing Sheets

OTHER PUBLICATIONS

Kikuchi, T., et al., "Ultrasonic Imaging System Using Interdigital Transducer," 1982 IEEE Ultrasonics Symposium, 0090–5607/82/0000–0618, pp. 618–622.

Matsunaka, T., et al., "Miniature Doppler Probe Using a Unidirectional Saw Transducer," Aloka Co., Ltd. 3–7–19 Imai Ohme, Tokyo 189, Japan, 4 pp.

Nomura, Tooru, et al., "Measurement and Mapping of Elastic Anisotropy of Solids Using a Leaky Saw Excited by an Interdigital Transducer," IEEE Transactions on Sonics and Ultrasonics, vol. SU–32, No. 2, Mar. 1985, pp. 235–240.

Moriizumi, Toyosaka, et al., Abstract, "Selection of Piezoelectric Materials Used for Interdigital Transducer in Water," The Transactions of the IECE of Japan, vol. E65, No. 5, May 1982, p. 288.

Nomura, T., et al., "Two Dimensional Mapping of Saw Propagation Constants by Using Fresnel–Phase–Plate Interdigital Transducer," 1983 IEEE Ultrasonics Symposium, pp. 621–626.

Sanghvi, N.T., et al., "Frequency Scanning, Front Viewing, Alternating Polarity Transducer Array for Ultrasound Imaging System," SPIE (International Society for Optical Engineering), Reprinted from "New Developments in Ultrasonic Transducers and Transducer Systems," Jul. 21–22 1992, San Diego, California, vol. 1733, 5 pp.

Transonic Systems Inc. Brochure, "Ultrasonic Transit–Time Volume Flowmeters," Oct. 1991, 2 pp.

Drost, Cornelis J., "Vessel Diameter–Independent Volume Flow Measurements Using Ultrasound," Proceedings of the San Diego Biomedical Symposium, vol. 17, 1978, 4 pp.

Mehdian, M., et al., "Blood Flow Measurement Using a Highly Filled Carbon Polymer Sandwich Sensor and an Elasto–Pseudo Compressible Vascular Flow," Part H, Journal of Engineering in Medicine, vol. 210, 1996, 8 pp.

Data Sciences International, Inc. Brochure, "Data Acquisition, Dataquest™ A.R.T.™, Advanced Research Technology Data Acquistion Platform & System, For Continuous and/or Scheduled Collection, Viewing, and Analysis of Physiological Data," SMD30043 REL01 Apr. 97, 4 pp.

Data Sciences International, Inc. Brochure, "PhysioTel©, CA, ETA and CTA Implants, For Measuring a Biopotential, Temperature and Activity," Brochure SMD30039 REL01 Oct. 1995, 2 pp.

Toda, Kohji, et al., "Acoustic Focusing Device With an Interdigital Transducer," J. Acoust. Soc. Am., vol. 62, No. 4, Oct. 1977, pp. 1033–1036.

Transonics Systems Inc. Brochure, "Ultrasonic Transit Time Theory of Operation," 2 pp.

TO POWER SUPPLY
AND MONITORING
CONSOLE

ULTRASONIC SENSORS FOR MONITORING THE CONDITION OF A VASCULAR GRAFT

This application is a divisional application, based on prior copending application Ser. No. 08/949,413, filed on Oct. 14, 1997, and now U.S. Pat. No. 5,807,258, the benefit of the filing date of which is hereby claimed under 35 U.S.C. § 120 and 37 C.F.R. § 1.53.

FIELD OF THE INVENTION

The present invention generally relates to the use of ultrasonic transducers to monitor flow and velocity, and more specifically, to the use of such sensors to monitor flow and velocity of blood through a graft, so as to determine the condition of the graft.

BACKGROUND OF THE INVENTION

A section of the vascular system in a patient's body that is diseased or defective can be surgically excised and replaced with a graft. A graft may comprise a portion of another vessel extracted from a different location in the patient's body or may be fabricated from an artificial, biocompatible material, such as GORTEX™ graft material, that will not be rejected by the patient's body. Although arterial grafts are often surgically implanted within the thorax of a patient, they may also be employed in other portions of the body. For example, an arteriovenous access graft or shunt is a specific type of graft employed to interconnect an artery and a vein and is typically disposed just below the skin in a patient's arm so that it is readily accessible for use in hemodialysis, i.e., to couple a patient suffering from renal failure to a dialysis machine.

Once a graft is surgically implanted, it is difficult to monitor its condition within a patient's body. Grafts often fail after a period of time due to the build up of blocking deposits, thromboses, or tissue growth within the internal lumen of the graft or at its junctions with the vessel in which it is inserted. It is estimated that the majority of arteriovenous access grafts used for hemodialysis will fail within about one year following their installation. In many cases, steps may be taken to restore full fluid flow through a graft that is becoming restricted—but only if the preventive measures are taken before the problem proceeds too far to be corrected without replacing the graft. Since it is generally not possible to determine the condition of flow through a graft without invasive surgery to inspect it, the procedure commonly adopted in the case of access grafts is to simply replace the graft each year, as a form of preventive maintenance. Clearly, it would be preferable to monitor the condition of a graft without resorting to invasive surgical procedures, so that the useful life of the graft can be extended and so that problems that may arise due to the failure of a graft can be avoided.

The best indicators of the condition of a graft are the velocity and volume of blood flowing through it. Fluid pressure at the distal and proximal ends of a graft (relative to the direction of blood flow) are a further indication of a graft's condition. As the lumen through a graft gradually becomes occluded with fatty buildup or other deposits, the pressure differential across the graft will increase, the velocity of blood in the lumen will decrease, and the flow of blood through the lumen will decrease. Each of these parameters thus serves as an indication of the condition of the graft and its viability to support necessary blood flow.

Ideally, it would be desirable to employ a graft—either natural or artificial—that includes means for monitoring the condition of fluid flow through the graft. The monitoring might occur continually or only periodically, upon demand. The means used for monitoring the condition of a graft should enable a physician to evaluate the parameters noted above at a remote location outside the patient's body, without resorting to an invasive procedure. Further, the monitoring means should at least periodically be supplied power from an external source, since it is unlikely that a battery could provide the power required by sensors and circuitry on the graft for an extended period of time.

Various techniques are known in the prior art for monitoring flow and velocity of a fluid inside a blood vessel, but in each case, the devices employed for this purpose are intended for relatively short-term use immediately following surgery and are not acceptable for the extended period for monitoring fluid flow, as noted above. For example, one type of volume flow measurement system described in U.S. Pat. No. 4,227,407 uses two piezoelectric ultrasonic transducers that are alternately activated to produce ultrasonic waves. The ultrasonic waves pass into a vein or artery and are modified by the flow of blood in the vessel interposed between the two transducers. When one transducer is actively transmitting an ultrasonic wave, the other transducer serves as a receiver of the wave. The two transducers are oriented at an acute angle relative to the longitudinal axis of the blood vessel, so that the ultrasonic sound wave propagating through the blood vessel has a component in the direction (or opposite to the direction) of blood flow through the vessel. In an alternative embodiment disclosed in this patent, the transducers are located on the same side of the blood vessel, spaced apart along its longitudinal axis, and a reflective plate is disposed on the opposite side of the vessel, intermediate the positions of the two transducers. An ultrasonic wave transmitted from either transducer passes through the blood vessel, is reflected from the reflective plate, and is received by the other transducer. The difference in the transit times for the sound waves transmitted from the two transducers (in both embodiments) is indicative of the flow through the blood vessel. If transducers used only extend over a small portion of the diameter of the vessel, the difference in transit time would be indicative of the velocity of blood flowing in the blood vessel. However, since the transducers shown in this prior art reference are sufficiently large so that the diameter of the blood vessel is fully encompassed by the sound waves the transducers emit, the transit time is indicative of the flow of blood flowing through the vessel, i.e., volumetric flow. The flow is thus determined without any consideration of the internal cross-sectional area of the blood vessel. While this prior art apparatus is useful for monitoring blood flow (or velocity) through a blood vessel that is surgically exposed, the transducers are too large to be implanted within a patient's body and are unsuitable to remain attached to or be incorporated into a graft to monitor the fluid flow status of the graft. Also, to provide a good acoustic path between the transducers and the adjacent surface of the vessel, it may well be necessary to apply the transducers against the surface of the vessel with sufficient force to distort the wall of the vessel into the notch in the apparatus that is formed adjacent the sloping face of each transducer. Such distortion of the vessel may adversely affect the accuracy of the measurements and is undesirable over an extended period of time.

Another prior art approach for determining the velocity and/or flow of blood in a vessel employs Doppler sensing using either a pulsed or continuous wave ultrasonic signal that is emitted at a defined angle relative to the longitudinal axis of the blood vessel. If only a single transducer is used, the angle must be accurately known, and any error in the angle must be corrected. However, if a transmitting transducer is disposed on one side of the blood vessel and a receiving transducer is disposed on the opposite side of the blood vessel, angled so that the ultrasonic beam reflected from the blood flowing through the vessel is directed to the receiving transducer, an angle correction is not required.

Examples of apparatus for Doppler monitoring of blood flow are disclosed in U.S. Pat. Nos. 5,289,821 and 5,588, 436. In the first of these two patents, an ultrasonic transducer wire assembly is secured to a strip of biologically inert or absorbable material, which is wrapped around and in contact with a blood vessel to form a cuff, preferably disposed downstream from an anastomosis of the vessel, such as may be performed during microvascular surgery. The wire from the transducer exits the patient's body through a slit and is coupled to ultrasonic processing means that determine the velocity of blood flowing through the vessel by the Doppler processing of an ultrasonic wave that is transmitted by the transducer and received as a reflection from the blood in the vessel. After monitoring the velocity of blood flow for about three to seven days to determine if any thromboses has formed that would impede blood flow, the wire and transducer can be pulled from the strip and removed from the body through a small incision, leaving the strip behind. This device is not usable for an extended period of time (much beyond seven days), since the slit in the skin where the wires penetrate represents a pathway for infection. Further, the patent teaches that the invention is primarily intended for use on blood vessels close to the skin surface, such as those resulting from microvascular surgery on a patient's hand and thus would be unusable for monitoring the fluid flow through grafts deep within a patient's body.

In the second patent listed above, a Doppler scheme for determining blood velocity in a vessel is disclosed, wherein an elongate sheath is provided with a transducer head at its distal end. Two wires extend longitudinally through the sheath to a transducer that is mounted preferably at an angle of about 45° relative to the longitudinal axis of the sheath. A biocompatible material such as epoxy encases both the transducer and the distal ends of the wires. This molded housing for the transducer has a concave surface that fixes the transducer relative to the blood vessel and provides a close fit to the surface of the blood vessel to provide a path for ultrasonic sound waves produced by the transducer to enter the blood vessel and for reflected waves to be detected by the transducer. A mesh band is wrapped around the transducer, and its ends are sutured together to hold the concave surface of the material in contact with the outer surface of the blood vessel. The band is made of VICRYL™ mesh or other absorbable/inert material. A thread having ends that run inside and along the longitudinal axis of the sheath secure the band to the distal end of the sheath. The proximal end of the sheath is preferably left extending through the patient's skin after the device is installed to monitor blood velocity through a vessel in contact with the concave surface of the material at the distal end of the probe. After the measurements are concluded (purportedly, after a maximum of up to 21 days), the thread is cut and pulled from its engagement with the band, so that the transducer, wires, and sheath can be withdrawn, leaving the band in place— possibly to be absorbed, depending on the material from which the band is fabricated.

Each of the Doppler devices discussed above is used to monitor the velocity of blood through a vessel, and to the extent that the cross-sectional area of the vessel is assumed or known, the devices enable flow to be estimated. However, neither prior art Doppler device is intended to monitor flow or velocity of blood for more than a few days. In addition, the elongate sheath used with the latter device is relatively bulky and not suitable for installation where available space around the vessel or graft is limited. Both devices put the patient at risk of infection, because at least the wires coupled to the transducer must extend from inside the patient's body through the skin, to an external monitoring system.

Another prior art technique for monitoring flow with a Doppler system that is more compact than the devices discussed above is based on a surface acoustic wave (SAW) transducer that couples a "leaky wave" into the wall of a blood vessel. The SAW transducer includes pairs of interdigital electrodes fabricated on a piezoelectric substrate that is relatively small, e.g., about 1.6 mm by 2.2 mm. This transducer is described in a paper entitled "Miniature Doppler Probe Using a Unidirectional SAW Transducer" by T. Matsunaka and S. Yamashita. To produce a unidirectional interdigital SAW transducer, the drive signal applied to half of the electrodes is phase shifted by 90° relative to that applied to the other electrodes. The ultrasonic waves produced by the device propagate primarily in only one direction at an angle, $\theta$, thereby enabling the direction of fluid flow in a blood vessel to be determined. The wave that would normally be transmitted in the opposite direction at an angle, $-\theta$, is instead canceled by the interference between the interdigital electrodes driven with signals that are phase shifted relative to each other. This prior art reference states that the signal produced by a prototype SAW transducer had a maximum amplitude at a radiation angle of about 54.5°, with a beam width of about 2.5 times the actual electrode width (one mm) and suggests that the beam width might be reduced by modifying the electrode layout to achieve a "focusing effect."

Several advantages of the interdigital electrode SAW transducer design relative to the other devices available to measure flow and velocity of blood through a graft are apparent. The interdigital SAW transducer is substantially smaller in size than the prior art devices and requires less energy to produce ultrasonic waves. Further, the beam width is substantially wider than the physical size of the electrodes so that the apparatus can be made relatively small compared to the size of the beam that it produces. In addition, unlike the single transducer apparatus shown in the prior art first discussed above, which produce both forward and rearwardly directed waves that are affected by the velocity of blood in either direction but cannot determine the direction of flow, the unidirectional SAW transducer is able to monitor fluid velocity and determine the direction of the fluid flow.

The prior art does not disclose an interdigital transducer that monitors transit time. Instead, each of the interdigital transducers of the prior art SAW transducer discussed above produces a leaky SAW wave and employs the Doppler effect to determine the velocity of blood in a vessel. For monitoring velocity and flow through a graft, it would be preferable to employ a transducer that is compact, like an interdigital SAW transducer, but one that also has the ability to measure transit time and thus flow, generally independent of any considerations of velocity profile or cross-sectional area of the graft. This transducer should be implantable, preferably built into or secured to the graft when the graft is installed in a patient's body, supplied with electrical power from a source outside the patient's body, without using wires that penetrate the dermal layer, and should also permit monitoring of the flow, velocity, and pressure of a fluid without use of wires that pass through the skin. Currently, no compact prior art device is available that can remotely monitor flow and velocity parameters of an implanted graft for long periods (e.g., for months or even years) of time. Further, none of the prior art devices is designed to be wholly implanted, remotely monitored, and provided with power from a remote source outside the patient's body.

SUMMARY OF THE INVENTION

In accord with the present invention, a graft adapted to be coupled into a patient's vascular system is defined that includes a biocompatible material formed into a generally cylindrical shape and having a circular wall defining a lumen extending along a longitudinal axis. The lumen is adapted to convey a fluid through the graft. A first transducer is disposed within the wall of the graft and produces a signal indicative of a parameter of the fluid that is flowing through the lumen. Coupled to the first transducer is an antenna coil for conveying the signal to a point external to the patient's body, so that the signal is usable for evaluating a condition of the graft.

In one embodiment of the invention, the first transducer comprises a first pressure sensor, and the signal that it produces is indicative of a pressure of the fluid in the lumen. Preferably, the graft includes a second pressure sensor that is disposed within the wall of the graft, also producing a signal indicative of the pressure of the fluid in the lumen. Since the first and second pressure sensors are disposed adjacent opposite ends of the graft and monitor the pressure of the fluid in the lumen at each end, they enable a differential pressure to be determined as an indication of the condition of the graft.

In another embodiment, the first transducer includes a plurality of elements formed on a piezoelectric substrate. When excited by a radio frequency signal, the elements emit ultrasonic waves that propagate into the lumen and are affected by the fluid flowing through the lumen. The graft also includes a receiver, which responds to the ultrasonic waves by producing the signal indicative of the parameter. The receiver is coupled to the coil so that the signal produced by the receiver is conveyed outside the patient's body. For this embodiment, the parameter is either a velocity or a flow of the fluid through the lumen of the graft. The signal indicative of the parameter is determined as a function of the fluid's effect on the ultrasonic waves within the lumen.

In one form of the invention that employs the ultrasonic waves, the receiver comprises a second transducer that includes a plurality of elements formed on a piezoelectric substrate. The second transducer is also disposed within the wall of the graft and responds to the effect that the fluid in the lumen has on the ultrasonic waves to produce the signal indicative of the parameter. The first transducer and the second transducer are disposed on opposite sides of the graft, so that the ultrasonic waves pass through the lumen when traveling between the two transducers. The signal produced by the second transducer thus provides an indication of a transit time of the ultrasonic waves through the lumen. Preferably, the plurality of elements comprising the first transducer and the second transducer are sufficiently flexible to conform to a curved shape of the wall.

Also, the plurality of elements comprising the first transducer are divided into a first portion and a second portion. The elements comprising the first portion are interdigitally dispersed among elements comprising the second portion and are adapted to couple to the radio frequency signal in one polarity, while the elements comprising said second portion are adapted to couple to the radio frequency signal in an opposite polarity. As a result, the ultrasonic waves produced by the elements comprising the second portion are phase shifted by about 180° relative to the ultrasonic waves produced by the elements comprising the first portion.

A phase shifter is included in one embodiment. For this embodiment, the elements comprising the first transducer are divided into four portions arranged in an ordered array in which each successive element is from a different one of the four portions, taken in order. The radio frequency signal is applied to the phase shifter, and a phase shifted signal produced by the phase shifter is applied to at least two of each successive four elements to provide about a 90° phase difference between the ultrasonic waves emitted by successive elements. Thus, the ultrasonic waves that are emitted by the first transducer in one direction are substantially canceled due to a destructive interference.

In another form of the invention, the first transducer and the second transducer are spaced apart from each other along a side of the graft. A reflector is disposed on an opposite side of the graft from the first transducer and generally opposite a point between the first transducer and the second transducer. The ultrasonic waves from the first transducer pass through the lumen and are reflected back toward the second transducer by the reflector.

Yet another form of the invention provides that the first transducer and the second transducer alternately function as an emitter and as a receiver of the ultrasonic waves during successive time intervals. The radio frequency signal is coupled to the plurality of elements comprising the second transducer when the second transducer functions as the emitter of the ultrasonic waves. During this time, the plurality of elements comprising the first transducer are coupled to the coil and produce the signal indicative of the parameter, in response to the ultrasonic waves passing through the lumen. A multiplexer is used for alternately coupling the first and the second transducers to the radio frequency signal and to the coil.

The frequency of the radio frequency signal is preferably controlled to determine a beam angle along which the ultrasonic waves are emitted by the first transducer.

To provide electrical power for energizing electrical components of the graft, the coil is adapted to couple to a source of energy that is external to the patient's body. In one embodiment, the coil is disposed within the wall of the graft. In this form of the invention, the coil may comprise a mesh of insulated wire formed in a plurality of loops. The coil may be generally saddle shaped, substantially conforming to a curvature of the wall about the longitudinal axis of the graft. Further, the coil is preferably adapted to electromagnetically couple to an external coil that is connected to the source of energy.

When the first transducer comprises the receiver, the radio frequency signal is applied to the plurality of element as a pulse, causing the plurality of ultrasonic waves to be emitted as a pulse. The elements comprising the first transducer then receive an echo of the pulse of ultrasonic waves that is reflected from the fluid. This echo is employed to determine the parameter based on a Doppler effect.

Another aspect of the present invention is directed to a system for monitoring a parameter indicative of a condition of a vessel relating to its ability to convey a fluid. The system includes a carrier band that is adapted to couple about the vessel in close proximity to at least one side of the vessel. A first transducer having a plurality of conformal elements is disposed in a spaced-apart array on the carrier band. The plurality of conformal elements are sufficiently flexible and are shaped so that they are adapted to curve about the vessel, conforming to its shape. The first transducer is adapted to couple to a radio frequency signal and produces ultrasonic waves when excited by the radio frequency signal. The ultrasonic waves are emitted from the plurality of conformal elements and are directed into an interior of the vessel. A receiver is disposed to receive the ultrasonic waves after they have propagated at least partially through the vessel. The receiver produces a signal indicative of an effect on the ultrasonic waves due to the fluid in the vessel. A coil is coupled to the receiver for transmitting the signal produced by the receiver outside the patient's body.

Other aspects of the present invention are directed to methods that include steps that are generally consistent with the functions implemented by components of the apparatus discussed above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

The present invention is employed for monitoring the status of fluid flow through a vessel and is disclosed in connection with a preferred application in which the flow through a graft that has been implanted in a patient's vascular system is monitored. However, it is not intended that the invention be limited to that application. Although much of the following disclosure relates to that medically related application of the invention, it is also contemplated that various aspects of the present invention are also applicable to monitoring the status of fluid flow through any type of vessel, including without limitation, fluid flow through a vessel employed in an industrial process.

Employment of the present invention in the above-noted medical application addresses the problems noted above in the Background of the Invention. Specifically, if the status of fluid flow through a graft that has been implanted in a patient's vascular system is to be monitored for an extended period of time, the system used for this purpose will very likely need to receive energy from an external source and must convey data indicating the status of fluid flow through the implanted graft to an external monitoring device that is disposed outside the patient's body. In many cases, it may be desirable to monitor the status of flow through multiple grafts or at multiple locations on a single graft. Thus, the data signal indicating the status of fluid flow sensed by each separate transducer must be selected to monitor the condition of fluid flow at each location of a transducer. However, in some cases, only a single transducer may be required to monitor a parameter such as flow or velocity, which is indicative of the internal condition of the graft.

Figure 1:
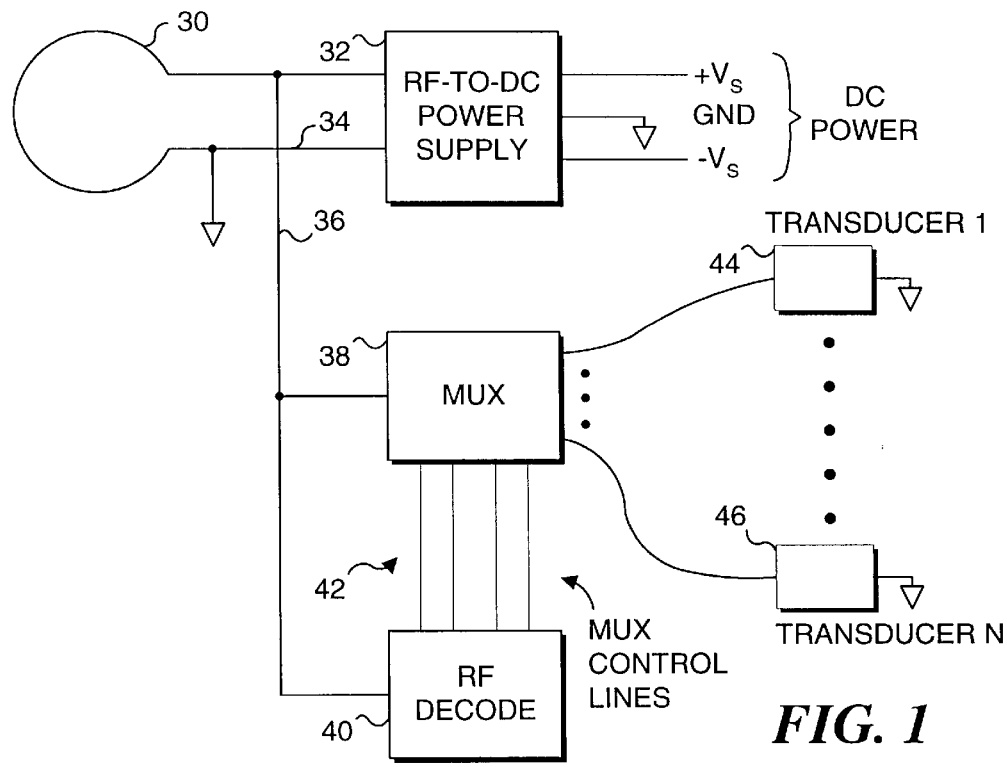
FIG. 1 is a block diagram showing a first embodiment of an implanted electronic circuit for monitoring the status of a graft with a selected transducer from a plurality of transducers.

FIG. 1 illustrates a first embodiment of an implanted electronics system for monitoring flow, applicable to the situation in which n transducers are included on one or more grafts implanted in the patient's body. Variations of the electronic circuit shown in FIG. 1 are discussed below to accommodate specific conditions. In addition, other embodiments of electronic circuits are illustrated in FIGS. 2–6. These embodiments, like that of FIG. 1, are useful for providing power to transducers that monitor fluid flow or velocity through a graft, and for transmitting data signals from the transducers outside a patient's body to an external remote monitoring console. Some of these circuits are better suited for certain types of measurements than others, and again, variations in the implanted electronic circuits are discussed below, as appropriate.

Each of the circuits shown in FIGS. 1–6 are intended to be implanted within the patient's body and left in place at least during the period in which the flow conditions through one or more grafts are monitored to determine the status of the graft. Although separate functional blocks are illustrated for different components of the implanted electronic circuits in these Figures, any of the implanted electronic circuits can be implemented in one or more application specific integrated circuits (ASICs) to minimize size and cost, which is particularly important when the electronic circuits are integral with a graft. The implantable electronic circuits can be either included within the wall of a graft in the case of a synthetic (i.e., man-made) graft, or may be simply affixed to or implanted adjacent to the graft for either man-made grafts or natural grafts that comprise a portion of a vessel taken from a different location in the patient's circulatory system.

Each of the circuits shown in FIGS. 1–6 includes an RF coupling coil 30, which is connected through lines 34 and 36 to an RF-to-DC power supply 32. This power supply rectifies and filters an RF excitation signal supplied from an external source to RF coupling coil 30, providing an appropriate voltage DC power signal for the other components of the circuits illustrated in these Figures. In the simplest case, the RF-to-DC power supply would only require rectifiers and filters as appropriate to provide any needed positive and negative supply voltages, $+V_s$ and $-V_s$. However, it is also contemplated that the power supply may provide for a DC-to-DC conversion capability in the event that the electromagnetic signal coupled into RF coupling coil 30 is too weak to provide the required level of DC voltage for any component. This conversion capability would increase the lower voltage produced by the direct coupling of the external RF excitation signal received by the RF coupling coil, to a higher DC voltage. Details of the RF-to-DC power supply are not shown, since such devices are well known to those of ordinary skill in constructing power supplies. It is also contemplated that it may be necessary to limit the maximum amplitude of the RF input signal to the RF-to-DC power supply to protect it or so that excessive DC supply voltages are not provided to the other components. Alternatively, each component that must be provided with a limited DC voltage supply may include a voltage limiting component, such as a zener diode or voltage regulator (neither shown).

The RF-to-DC power supply may include a battery or a capacitor for storing energy so that it need not be energized when monitoring the flow status, or at least, should include sufficient storage capability for at least one cycle of receiving energy and transmitting graft status indicative data outside the patient's body. Although a storage battery can be included, size limitations may prohibit any significant storage capacity. Instead, a relatively small capacitor could provide the required storage capability. Neither a battery or power storage capacitor are illustrated in the Figures, since they are well known to those of ordinary skill and are only optional.

An additional element that is common to each of the circuits shown in FIGS. 1–6 is an RF decode section 40, which is used for generating control signals that are responsive to information encoded in the external RF excitation signal received by RF coupling coil 30. This information can be superimposed on the RF excitation signal, e.g., by amplitude or frequency modulating the signal received.

Figure 2:
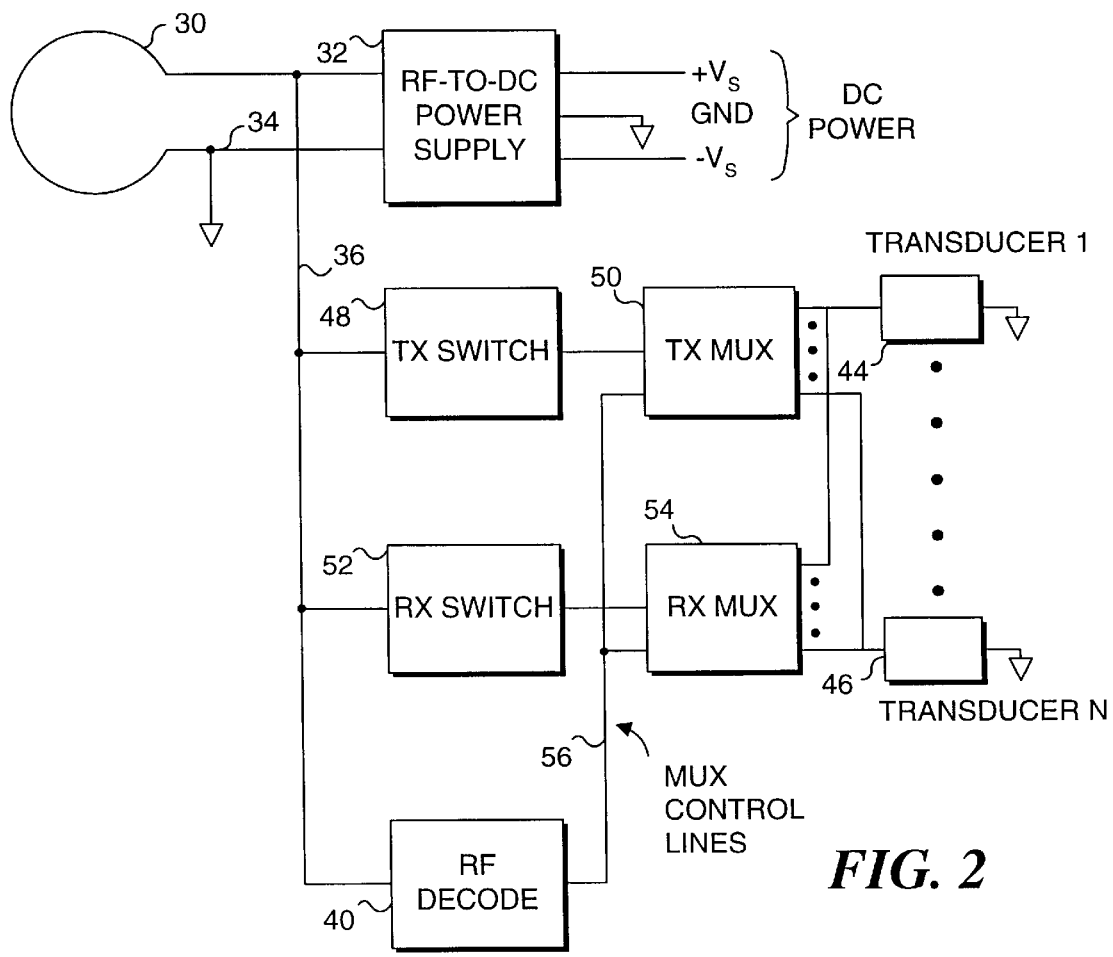
FIG. 2 is a block diagram of a second embodiment of an implanted electronic circuit for monitoring the status of a graft using separate multiplexers for transmit and receive functions.
Figure 3:
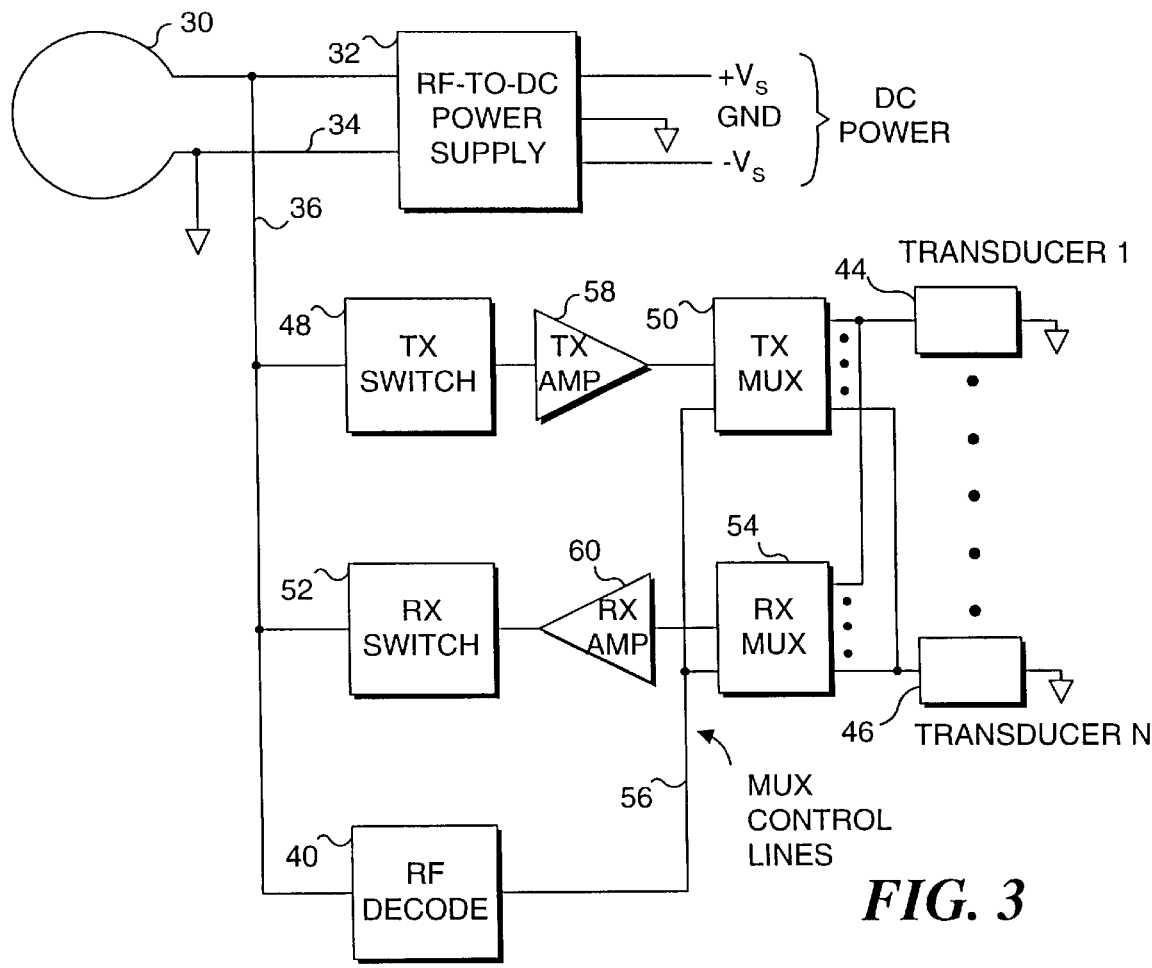
FIG. 3 is a block diagram of a third embodiment of an implanted electronic circuit for monitoring the status of a graft using separate multiplexers and amplifiers for transmit and receive functions.

In regard to the circuits shown in FIGS. 1–3, the RF excitation frequency is the same as the frequency used to excite a selected ultrasonic transducer to produce an ultrasonic wave that propagates through a vessel or graft being monitored, and for conveying data from a transducer that receives the ultrasonic waves. This approach generally simplifies the implantable electronic circuitry but may not provide optimal performance. Therefore, FIGS. 4 and 5 disclose implantable electronic circuitry in which the RF excitation frequency used to provide power to the RF-to-DC power supply and to provide control signals to RF decode section 40 is decoupled from the frequency that is used for exciting the transducers and modulating the data that they provide for transmission to a point outside the patient's body.

Details of the Implantable Electronic Circuits

Referring now to FIG. 1, line 36 from RF coupling coil 30 is connected to a multiplexer (MUX) 38 to convey signals from a selected one of a plurality of n transducers 44–46 that are coupled to the MUX. To select the transducer that will provide the data signal related to the status of flow through the graft being monitored, RF decode section 40 provides a control signal to MUX 38 through MUX control lines 42. The control signal causes the MUX to select a specific transducer that is to be excited by the RF signal received by RF coupling coil 30 and further, causes the MUX to select the transducer that will provide the data signal for transmission outside the patient's body via RF coupling coil 30.

In addition to ultrasonic transducers, the implantable electronic circuit shown in FIG. 1 can also be used in connection with pressure transducers. For ultrasonic transducers, the circuit is perhaps more applicable to the Doppler type for use in monitoring fluid velocity through a graft. If a single-vessel pulse Doppler transducer is used, the same transducer can be used for both transmission and reception of the ultrasonic wave, thereby eliminating the need for MUX 38. In the event that the transducers shown in FIG. 1 are used for transit time flow measurements, it will normally be necessary to use MUX 38 to switch between the transducer used for transmitting the ultrasonic wave and that used to receive the ultrasonic wave, which may present some problems in connection with switching speed, power consumption, and switching transient recovery.

For a single-vessel transit time measurement, a pair of opposed transducers that are disposed on opposite sides of the graft are typically used. In order to acquire bi-directional fluid flow data, the direction of the ultrasound wave propagation must be known, i.e., the direction in which the ultrasound wave propagates relative to the direction of fluid flow through the vessel. In this case, MUX 38 is required. However, for single-vessel applications in which the fluid flow is in a single known direction, the transducers that are disposed on opposite sides of the graft can be electrically connected in parallel or in series, eliminating any requirement for MUX 38. The RF-to-DC power supply and RF decode sections could also then be eliminated, since the retarded and advanced transit time signals would be superimposed on the same RF waveform transmitted by RF coupling coil 30 outside the patient's body. Although this modification to the implantable electronic circuit shown in FIG. 1 would not permit the direction of fluid flow through a graft to be determined, the retarded and advanced transit time signals would interfere as they propagate in time, and their interference can be used to estimate the magnitude of fluid flow through the graft.

In FIG. 2, an implantable electronic circuit is shown that uses a transmit multiplexer (TX MUX) 50 and a receive multiplexer (RX MUX) 54. In addition, a transmit (TX) switch 48 and a receive (RX) switch 52 couple line 36 to the TX MUX 50 and RX MUX 54, respectively. RF decode section 40 responds to instructions on the signal received from outside the patient's body by producing a corresponding MUX control signal that is conveyed to TX MUX 50 and RX MUX 54 over MUX control lines 56 to select the desired transducers.

When ultrasonic signals are being transmitted by one of the selected transducers 1 through n, a TX switch 48 couples the RF excitation signal received by RF coupling coil 30 to the transducer that is transmitting the ultrasonic signal, which is selected by TX MUX 50. The TX switch is set up to pass excitation signals to the selected transducer only if the signals are above a predetermined voltage level, for example, 0.7 volts. Signals below that predetermined voltage level are blocked by the TX switch. Similarly, a RX switch 52 connects the transducer selected by RX MUX 54 to RF coil 30 and passes only signals that are below the predetermined voltage level, blocking signals above that level. Accordingly, the RF signal used to excite a first transducer selected by TX MUX 50 passes through TX switch 48 and the lower amplitude signal produced by a second transducer selected by RX MUX 54 in response to the ultrasonic signal transmitted through the graft is conveyed through RX MUX 54 and RX switch 52 and transmitted outside the patient's body through RF coil 30.

The implantable electronic circuit shown in FIG. 3 is similar to that of FIG. 2, but it includes a transmit amplifier (TX AMP) 58 interposed between TX switch 48 and TX MUX 50, and a receive amplifier (RX AMP) 60 interposed between RX MUX 54 and RX switch 52. TX AMP 58 amplifies the excitation signal applied to the transducer selected by TX MUX 50 for producing the ultrasonic wave that is propagated through a graft. Similarly, RX AMP 60 amplifies the signal produced by the transducer selected by RX MUX 54 before providing the signal to the RX switch for transmission outside the patient's body. Again, the circuit shown in FIG. 3 is most applicable to transit time flow measurements and employs the same frequency for both the RF excitation signal that supplies power to RF-to-DC power supply 32 and the signal applied to a selected one of transducers 44–46 to generate the ultrasonic wave propagating through the graft.

Figure 4:
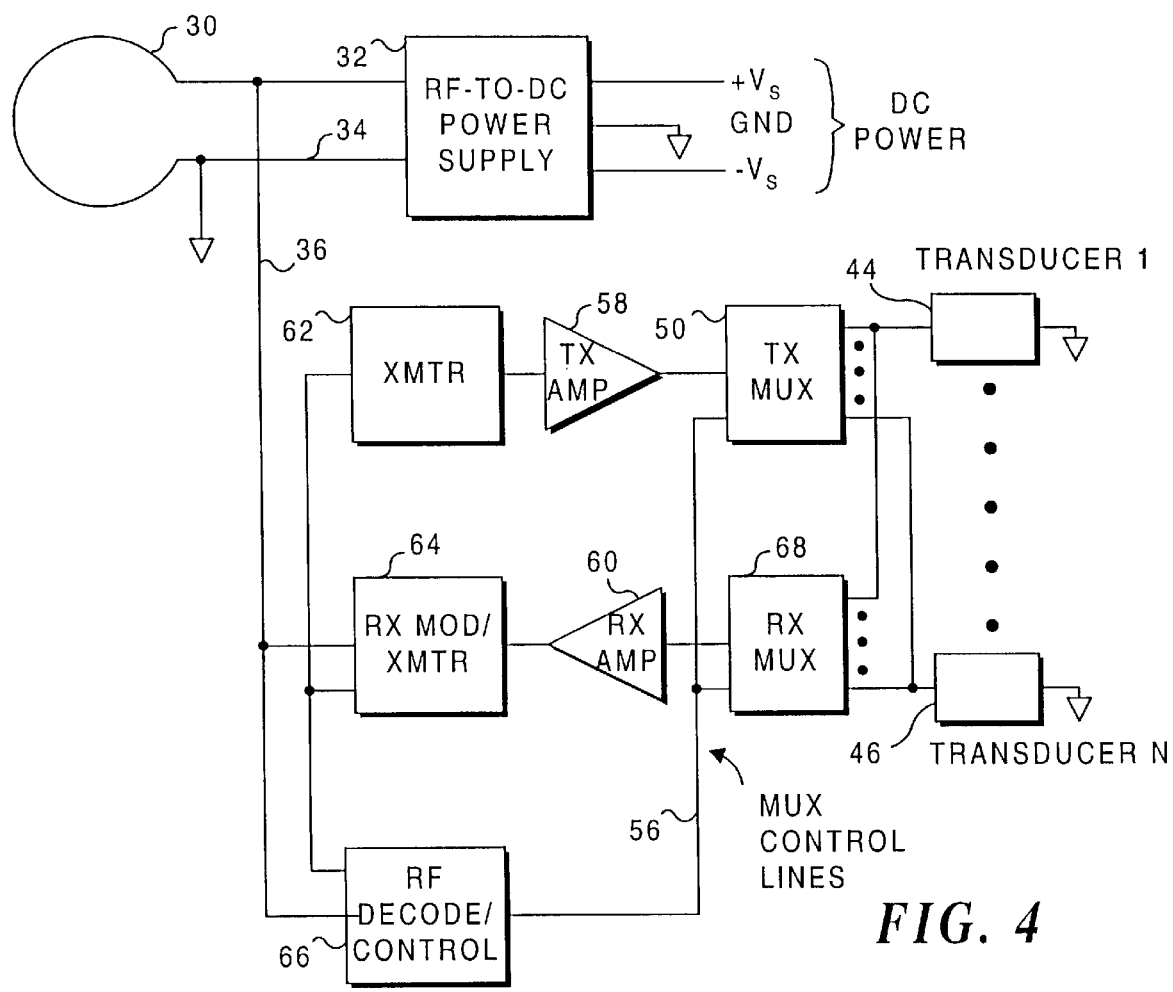
FIG. 4 is a block diagram of a fourth embodiment of an implanted electronic circuit for monitoring the status of a graft that employs a local transmitter to excite a selected transducer, and a modulator/transmitter for transmitting signals from the transducers.

In contrast to the implantable electronic circuits shown in FIGS. 1–3, the circuit shown in FIG. 4 enables the RF excitation frequency applied to RF-to-DC power supply 32 to be decoupled from the signal applied to excite any selected one of transducers 44–46. Similarly, the signal produced by the transducer receiving the ultrasonic waves propagating through the graft is at a different frequency than the RF excitation frequency. In FIG. 4, a transmitter (XMTR) 62 and a receive modulator/transmitter (RX MOD/XMTR) 64 are coupled to and controlled by an RF decode/control section 66. The RF decode/control section determines when the excitation frequency is generated for application to a selected transmit transducer and when the signal produced by the transducer selected to receive the ultrasonic wave is used for modulating the RF signal applied to RF coupling coil 30. An advantage of this approach is that the RF power delivered to RF coupling coil 30 is at an optimal frequency for penetration through the patient's body, thereby improving the efficacy with which the RF energy couples to a specific depth and location within the body. Another reason is for satisfying any requirements for selecting a particular frequency to comply with radio frequency allocation bands for medical equipment. Similarly, the frequency applied to any selected transducers 44 and 46 to stimulate their production of ultrasonic waves can be optimal for that purpose. Assuming that the two frequency bands, i.e., the RF excitation frequency band for the signal applied to the power supply and the frequency band applied to excite the transducers, are sufficiently separated, the RF power delivery can occur simultaneously with the excitation of a selected transducer and the reception of the ultrasonic waves by another selected transducer. Accordingly, more RF power can be coupled into the system from the external source than in the implantable electronic circuits shown in FIGS. 1–3.

The control signals that are supplied to RF decode/control section 66 via RF coupling coil 30 can be conveyed using nearly any kind of modulation scheme, e.g., by modulating the RF excitation that powers the device, or by sending a control signal on a separate and distinct RF frequency. Also, the signals that are received from the transducer in response to the ultrasonic wave that is propagated through the graft can be transmitted through the RF coupling coil at a different frequency than the incoming excitation frequency, thereby eliminating interference between the power supply and data signal transmission functions.

The implantable electronic circuit shown in FIG. 4 is most applicable to transit time flow measurements in which pairs of transducers are selected for transmitting and receiving the ultrasonic wave that propagates through the one or more grafts on which the transducers are installed. RF decode/control section 66 can be employed to control TX MUX 50 and RX MUX 68 to interchange the transducers used for transmission and reception of the ultrasonic wave on successive pulses. Using this technique, the direction of the ultrasonic wave propagation through the graft is changed on alternating pulses of ultrasonic waves, enabling transit time difference information to be gathered without requiring further multiplexer programming information to be transmitted between successive ultrasonic wave pulses. This approach greatly improves the data gathering efficiency of the implantable electronic circuit shown in FIG. 4 compared to the previously described implantable electronic circuits of FIGS. 1–3.

Figure 5:
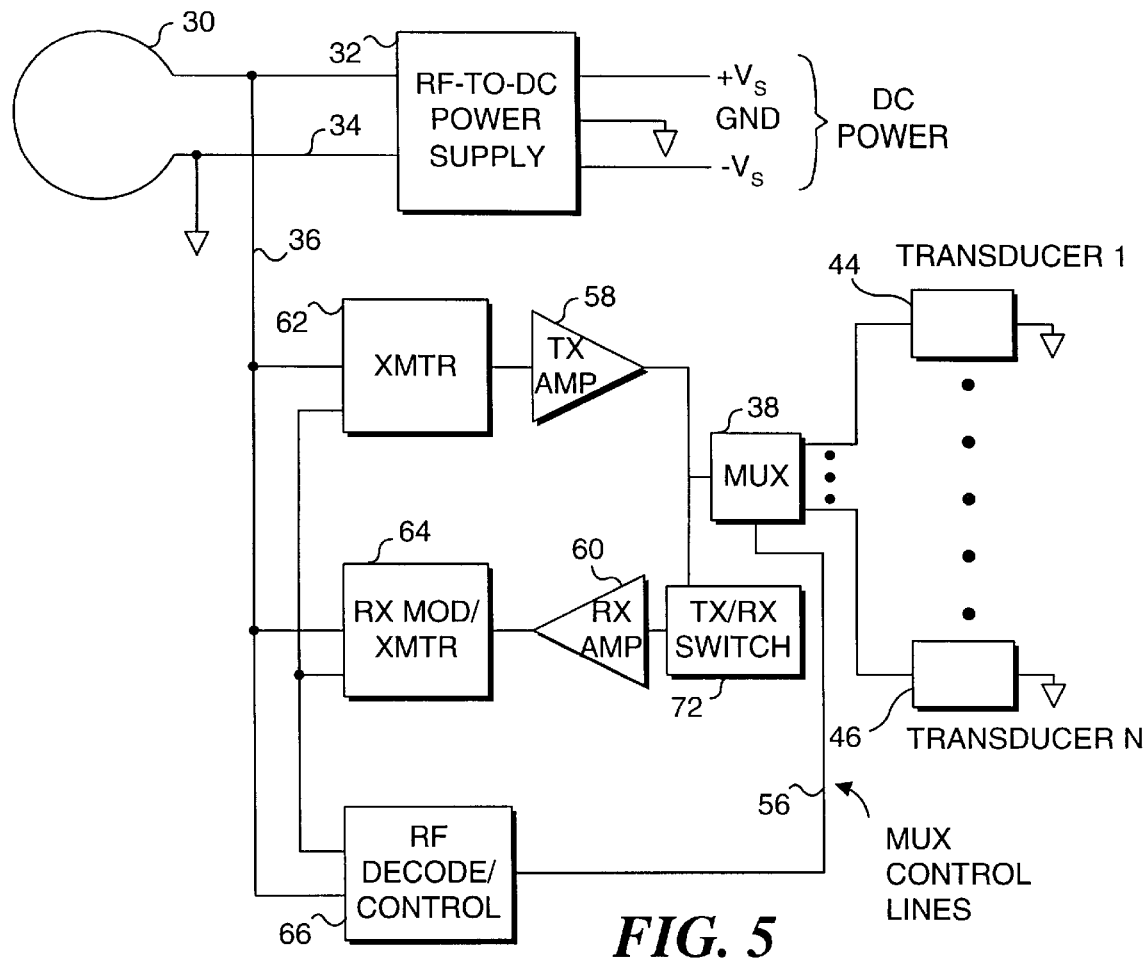
FIG. 5 is a block diagram of a fifth embodiment of an implanted electronic circuit for monitoring the status of a graft, where one transducer is selected for transmitting and receiving, and a modulator/transmitter is used for transmitting the signal produced by the receiving transducer.

To further improve the implantable electronic circuit shown in FIG. 4 for use in sensing fluid velocity through a graft using a Doppler technique, the modification shown in FIG. 5 is made. In the latter implantable electronic circuit, a TX/RX switch 72 is added so that the circuit transmits and receives through the same transducer. As a result, separate transmit and receive multiplexers are not required. Instead, MUX 38 is used to select the specific transducer for receiving the RF excitation signal produced by XMTR 62 so that the transducer produces an ultrasonic wave and then receives the echo from fluid flowing through the graft to produce a receive data signal that is output through RX MOD/XMTR 64. TX/RX switch 72 prevents the signal applied by TX AMP 58 from overdriving the input to RX AMP 60, effectively isolating the RX AMP during the time that the RF signal is applied to the transducer to excite it so that it produces the ultrasonic wave. However, the echo signal received by the transducer is allowed to reach RX AMP 60 when TX/RX switch 68 changes state (from transmit to receive). Generally, the implantable electronic circuit shown in FIG. 5 has the same benefits as described above in connection with the circuit shown in FIG. 4. RF decode/control section 66 responds to the information received from outside the patient's body that determines which one of transducers 44–46 is selected at any given time by producing an appropriate MUX control signal that is supplied to MUX 38 over MUX control lines 56.

It is also contemplated that RF decode/control section 66 may cause MUX 38 to select a different transducer for producing/receiving the ultrasonic waves after a predefined number of transmit/receive cycles have elapsed. For example, a different transducer may be selected after eight cycles have been implemented to transmit an ultrasonic wave into the graft and to receive back the echoes from the fluid flowing through the graft. By collecting data related to the status of flow through one or more grafts in this manner, it becomes unnecessary to send programming information to RF decode/control section 66 after each cycle of a transmission of the ultrasonic wave into the fluid in the graft and reception of the echo. By carrying out a predefined number of transmit/receive cycles for a given transducer that has been selected by MUX 38 and averaging the results, a more accurate estimate of fluid velocity through the graft can be obtained than by using only a single transmission and reception of an ultrasonic wave. Since the signal required to instruct RF decode/control section 66 to change to the next transducer is only required after the predefined number of cycles has been completed, the data gathering efficiency of the implanted electronic circuit is improved.

Figure 6:
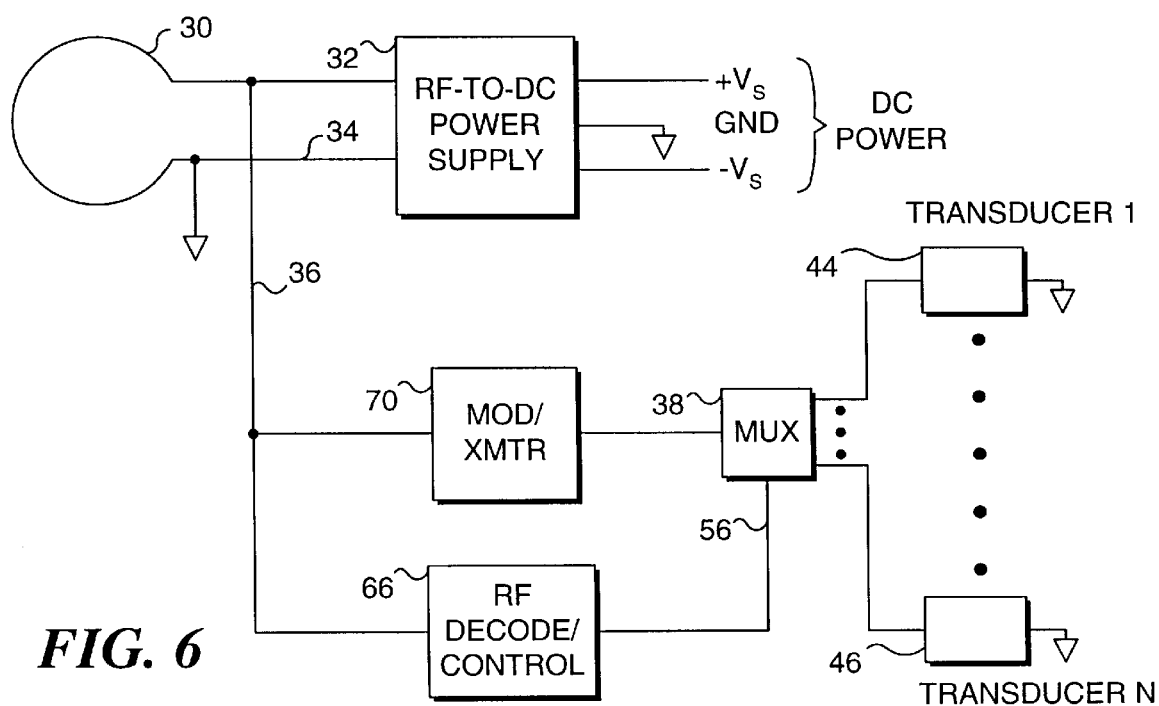
FIG. 6 is a block diagram of a sixth embodiment of an implanted electronic circuit for monitoring the status of a graft, wherein one of a plurality of transducers is selectively coupled to a modulator/transmitter for transmitting a signal indicative of fluid pressure or other parameters.

Although transducers 44–46 that are shown in FIGS. 1–5 need not be ultrasonic transducers, FIG. 6 illustrates an implantable electronic circuit that is particularly applicable for use with transducers 44–46 comprising pressure sensors. For example, such pressure sensors could be disposed within the wall of a synthetic graft to sense the pressure of fluid flowing through the graft at one or more points. MUX 38 is used for selecting a specific pressure transducer to provide a data signal that is transmitted to the outside environment via RF coupling coil 30. In this circuit shown in FIG. 6, a modulator/transmitter (MOD/XMTR) 70 receives the signal from the transducer selected by MUX 38 in response to the MUX selection signal provided over MUX control lines 56 from RF decode/control section 66 and using the signal, modulates an RF signal that is supplied to RF coupling coil 30. The RF signal transmitted by coupling coil 30 thus conveys the data signal indicating pressure sensed by the selected transducer. In many cases, it will be preferable to monitor the pressure at the distal and proximal ends of a graft in order to enable the differential pressure between these ends to be determined. This differential pressure is indicative of the extent to which thromboses or other source of blockage in the interior lumen of the graft is impeding fluid flowing through the lumen. In most cases, parameters such as fluid flow or velocity are better indicators of the status of flow through the graft.

RF Coupling Coil and External Coil Embodiments

FIGS. 7–12 illustrate details of several different embodiments for the RF coupling coil that is implanted within a patient's body for receiving RF energy to provide power for the implanted electronic circuits discussed above and for transmitting data relating to the condition of flow through one or more grafts that have been installed within the patient's vascular system. Optimization of RF coupling between the RF coupling coil that is implanted and the external coil is partially dependent upon the propagation characteristics of the human body. Since the body tissue is largely comprised of water, the relative dielectric constant of flesh is approximately equal to that of water, i.e., about 80. Also, the permeability of tissue comprising a body is approximately equal to one, i.e., about that of free space. The velocity of propagation of an RF signal through the body is proportional to the inverse square root of the dielectric constant and is therefore about 11% of the velocity of the signal in free space. This lower velocity reduces the wavelength of the RF signal by an equivalent factor. Accordingly, the wavelength of the RF signal transferred between the implanted RF coupling coil and the external coil would be a design consideration if the separation distance between the two is approximately equal to or greater than one-quarter wavelength. However, at the frequencies that are of greatest interest in the present invention, one-quarter wavelength of the RF coupling signal should be substantially greater than the separation distance between the two coils.

The penetration of RF fields in the human body has been studied extensively in conjunction with magnetic resonance imaging (MRI) systems. RF attenuation increases with frequency, but frequencies as high as 63 MHz are routinely used for whole-body imaging, although some attenuation is observed at the center of the torso at the upper end of the frequency range. In addition, MRI safety studies have also provided a basis for determining safe operating limits for the RF excitation that define the amplitude, which can be safely applied without harm to the patient.

It is contemplated that for graft implants placed deep within the abdomen of a patient, RF excitation and frequencies used for communicating data related to the fluid flow through a graft can be up to about 40 MHz, although higher frequencies up to as much as 100 MHz may be feasible. At 40 MHz, the wavelength of the RF excitation signal in tissue is about 82 cm, which is just that point where wavelength considerations become an important consideration. For shallow implants, RF excitation at a much higher frequency may be feasible. For example, access grafts that are used for hemodialysis are typically only about 5 mm beneath the surface of the skin, in the forearm of the patient. To provide energy to the implanted electronic circuit and to receive data from transducers associated with such grafts, frequencies in the range of a few hundred MHz may be useful. The dielectric properties of tissue have been studied to at least 10 GHz by R. Pethig, *Dielectric and Electronic Properties of Biological Materials*, Wiley Press, Chichester, 1979 (Chapter 7). Based on this study, no penetration problems are anticipated in the frequency range of interest. The dielectric constant of tissue decreases to about 60 at a frequency of 100 MHz and is about 50 at 1 GHz, but this parameter has little effect on power/data signal coupling.

Figure 7:
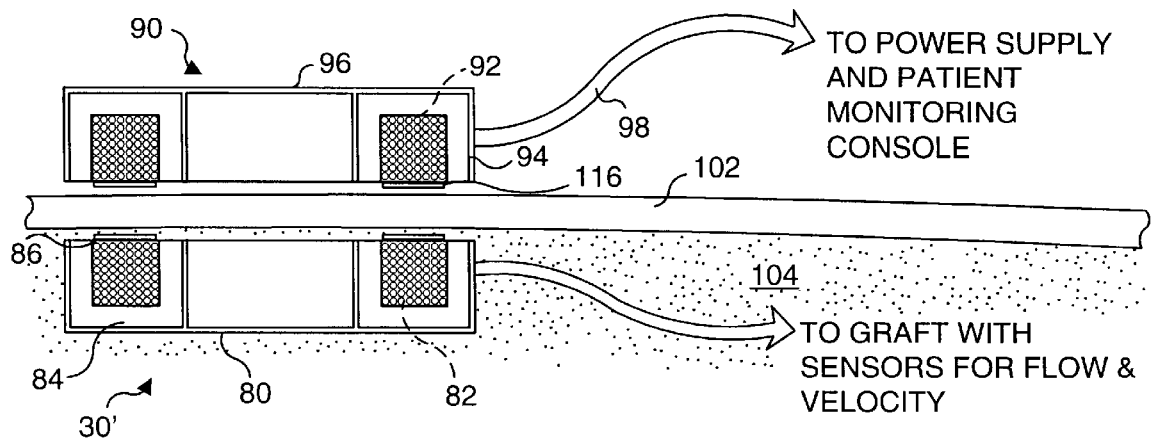
FIG. 7 is a cross-sectional view of an implanted radio frequency (RF) coupling coil and an external coil.

In FIG. 7, an RF coupling coil 30' is disposed opposite a corresponding external coil 90. RF coupling coil 30' includes a toroidal coil 82 that is wound in the hollow center channel of a toroidal shaped core 84. Core 84 and toroidal coil 82 are contained within a biocompatible housing 80 that also provides RF shielding around the coil except where it lies opposite to external coil 90. External coil 90 is of similar design, including a toroidal coil 92 disposed within the hollow center portion of a toroidal shaped core 94. A housing 96 comprising an RF shield encloses much of the toroidal coil and core. A cable 98 conveys signals to and from an external power supply and patient monitoring console 100, which is shown in FIG. 8.

Figure 8:
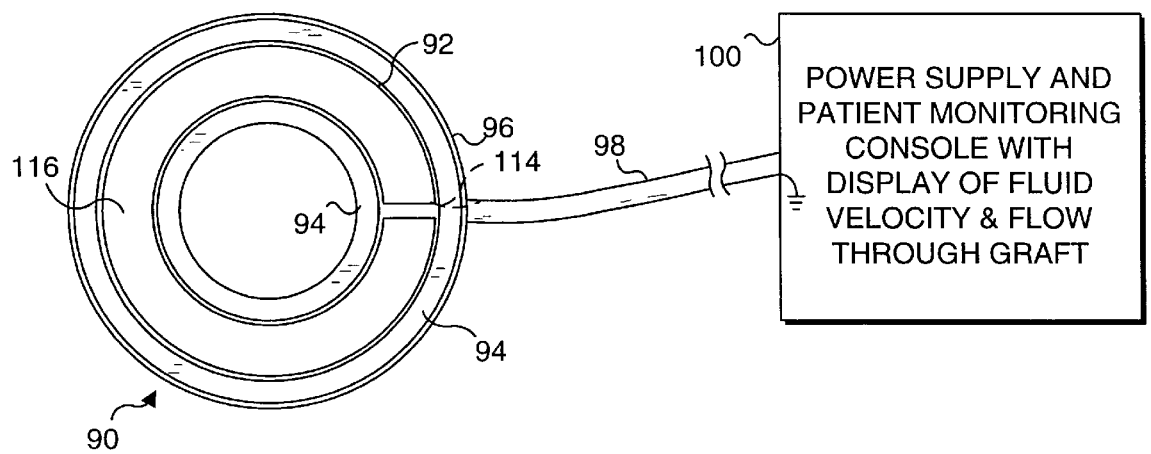
FIG. 8 is a bottom view of the external coil shown in FIG. 7.

The external coil and RF coupling coil shown in FIGS. 7 and 8 represent one embodiment used for coupling electrical energy and conveying data signals across a skin interface 102 for applications in which the RF coupling coil is implanted relatively close to the surface of the skin. For example, RF coupling coil 30' and external coil 90 would provide the coupling required for a system used to monitor coronary artery bypass grafts (CABG). During CABG surgery, a patient's chest is opened, making it relatively straightforward to implant RF coupling coil 30' beneath the skin as the chest is being closed at the conclusion of this surgical procedure.

Although the external core and internal core need not be identical in size and shape, it is generally true that coupling will be optimal if the annular surfaces of the two cores are of approximately the same dimensions and if the core halves are aligned. By observing the strength of the signal transmitted from RF coupling coil 30', it should be possible to position external coil 90 in proper alignment with the implanted coil so that the amplitude of the signal is maximized.

To function as a transformer core, the material used must have a relatively high magnetic permeability, at least greater than one. Although ferrite is commonly used for core materials, sintered powdered iron and other alloys can also be used. Since the choice of materials for the cores of the RF coupling coil and the external coil based on the magnetic characteristics of such materials are generally well understood by those of ordinary skill in the art, further details need not be provided herein to provide an enabling disclosure of the present invention.

Housing 96 on external coil 90 provides RF shielding against electromagnetic interference (EMI). Housing 96 is preferably conductive, grounded, and surrounds the external coil except where the face of core 84 is opposite core 94 of the implanted coupling coil. The RF shield comprising housing 96 also includes a split annular ring 116, which is attached to the internal shield (not separately shown) at cable 98. A similar split annular ring 86 is provided on RF coupling coil 30' covering toroidal core 82. Split annular rings 86 and 116 are used so that a shorted turn is avoided that would otherwise tend to attenuate a coupling between the external coil and RF coupling coil. The housing of the implanted coupling coil is connected to the shield on the cable, and the shield is connected to a shield on the graft. Inside power supply and patient monitoring console 100, the shield on cable 98 is connected to ground. The RF shields on both the external coil and the RF coupling coil that is implanted within the patient, along with the shields provided around the transducers (described below) minimize external EMI radiation due to the use of the present invention within a patient's body.

Figure 9:
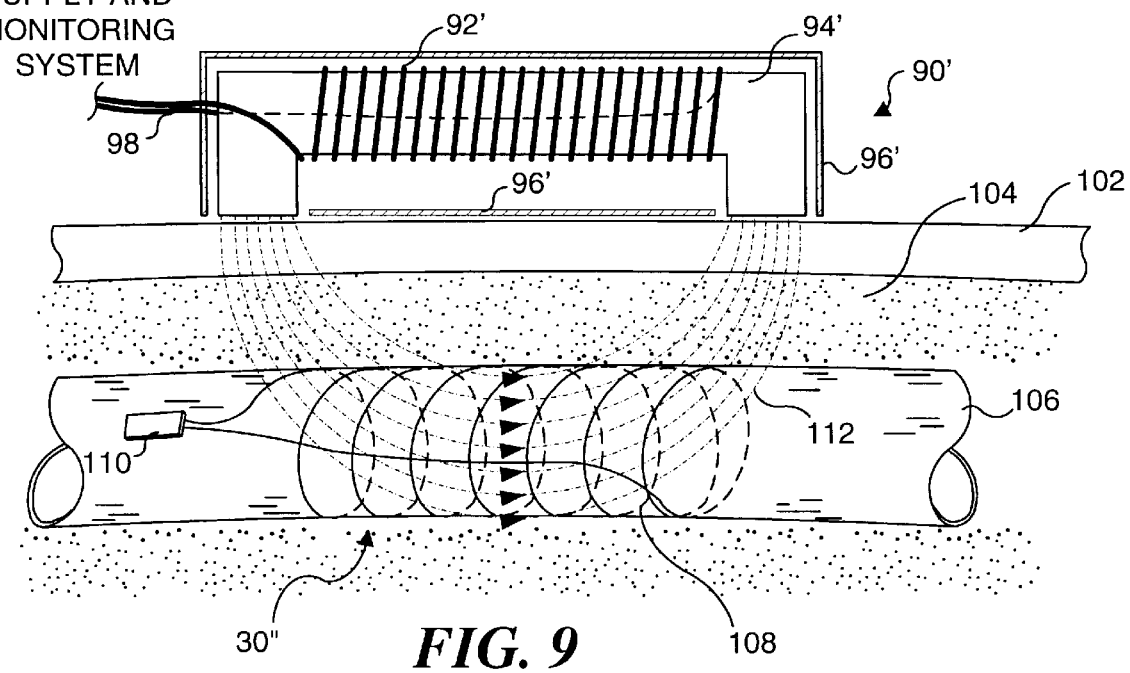
FIG. 9 is a cut-away side elevational view of an alternative external coil and a side elevational view of a graft, showing an integrated spiral RF coupling coil within the wall of the graft.

Referring now to FIG. 9, an RF coupling coil 30" is shown that comprises a plurality of spiral conductor coils 108 disposed within the wall of a graft 106. Although the drawing shows only a single layer of spiral coils 108, it is contemplated that a plurality of layers of such coils may be used and that the spacing between the spiral coils may be substantially closer than illustrated in the Figure. Coupling coil 30" is connected to an electronics assembly 110 that may include any of the implantable electronic circuits shown in FIGS. 1–6. Not shown in FIG. 9 are the transducers that are provided within the wall of or on the external surface of graft 106.

RF coupling coil 30" would typically be used in connection with a graft that is disposed relatively close to the outer surface of the patient's body, for example, within tissue 104 immediately below a dermal layer 102. In this disposition, the RF coupling coil more readily couples to an external coil 90'. External coil 90' shown in FIG. 9 has a generally C-shaped core 94' about which is coiled a plurality of turns 92'. Leads 98 pass through a housing 96' that comprises an RF shield and connect the external coil to a power supply and monitoring system (not shown). Lines of magnetic flux 112 intersect spiral coils 108 on RF coupling coil 30' to provide electrical power for energizing electronics assembly 110. Similarly, RF coupling coil 30" generates an EMI concentrated along the longitudinal axis of graft 106 that is sensed by external coil 90' to convey data indicating the flow status of the fluid through graft 106 to the power supply and monitoring system.

Core 94' of external coil 90' is preferably fabricated of a ferrite core material, or other suitable alloy. The number of coils 92', the size of the wire, size of the core, and other parameters can be determined for a particular frequency of operation using conventional transformer design criteria, by one of ordinary skill in the art.

Figure 10:
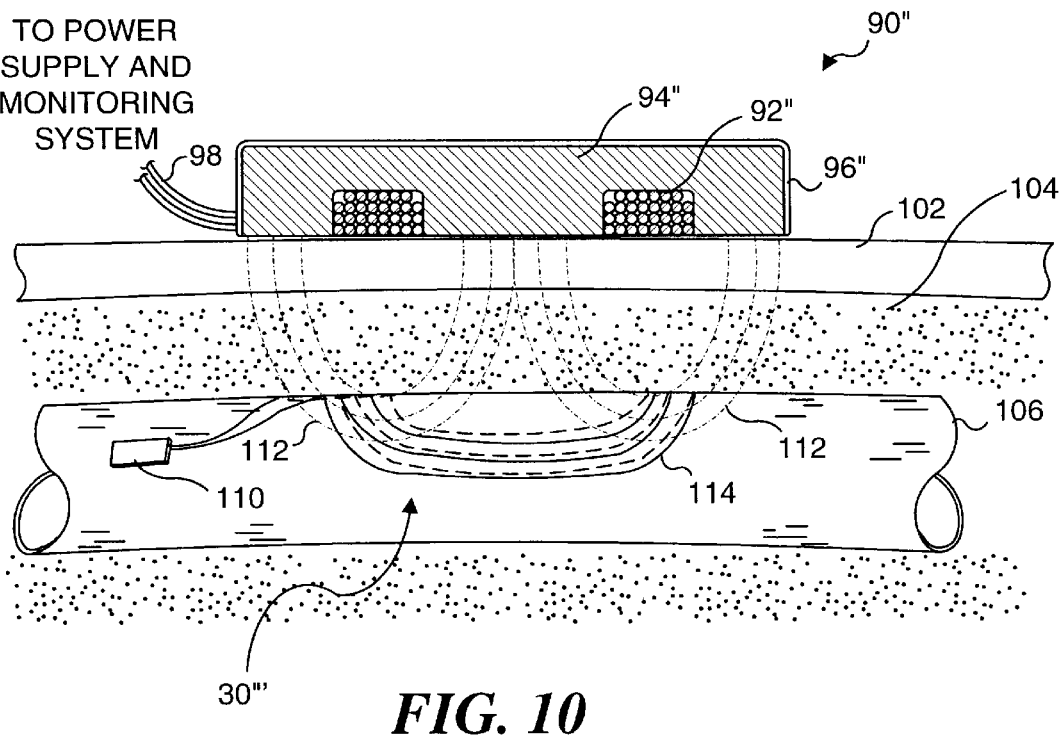
FIG. 10 is a cut-away side elevational view of a further embodiment of an external coil and a side elevational view of a graft that includes a saddle shaped integrated RF coupling coil within the wall of the graft.

In FIG. 10, an RF coupling coil 30'" is illustrated that comprises a plurality of generally saddle shaped coils 114 disposed within the wall of graft 106. Again, the RF coupling coil is coupled to electronics assembly 110. Although only a single layer of saddle shaped coils 114 is illustrated, it is contemplated that a plurality of such interconnected layers could be provided within the wall of the graft.

For use with RF coupling coil 30'", an external coil 90" is provided that includes a plurality of coils 92" wrapped around a central portion of a generally E-shaped core 94". Lines of electromagnetic flux are thus produced between the central leg and each of the end legs of core 94". It will therefore be apparent that this embodiment of the RF coupling coil and of the external coil achieve optimum coupling when the distance separating the two is minimal. Therefore, RF coupling coil 30'" and external coil 90" are best used in applications where graft 106 is disposed relatively close to dermal layer 102 so that tissue 104 separating the graft from external coil 90" is only a few centimeters thick. For example, this embodiment of the RF coupling coil and external coil is applicable for use with access grafts implanted just beneath the skin on the patient's forearm. Maximal coupling is achieved when the longitudinal axis of external coil 90" is aligned with the longitudinal axis of graft 106.

Figure 11:
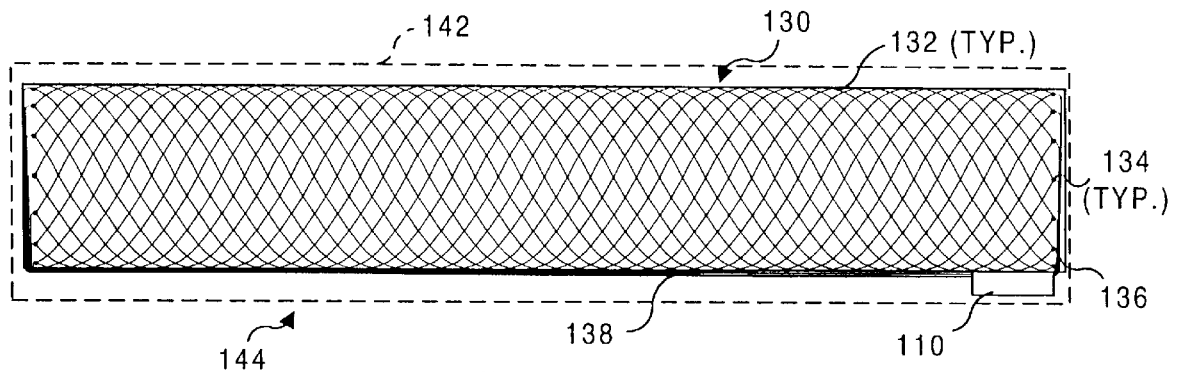
FIG. 11 is another embodiment of a woven spiral mesh RF coupling coil that is integrally provided in a wall of a graft.

A further embodiment of an RF coupling coil 130 that is disposed within a graft 144 is shown in FIG. 11. RF coupling coil 130 comprises a woven mesh 132 fabricated from insulated wire so that overlapping segments of the mesh do not electrically connect in the center of the graft. At each end of the RF coupling coil, the wires comprising wire mesh 132 are electrically coupled together, producing a multi-turn coil. If each wire comprising the mesh passes around the central axis of the graft through m degrees, and if there are a total of n such wires, then the equivalent number of turns in coupling coil 130 is equal to n×m÷360. Leads 136 and 138 convey signals to and from nodes 134, connecting the wire mesh to electronics assembly 110. A biocompatible coating 142 surrounds the mesh, protecting it from contact with bodily fluids.

Figure 12:
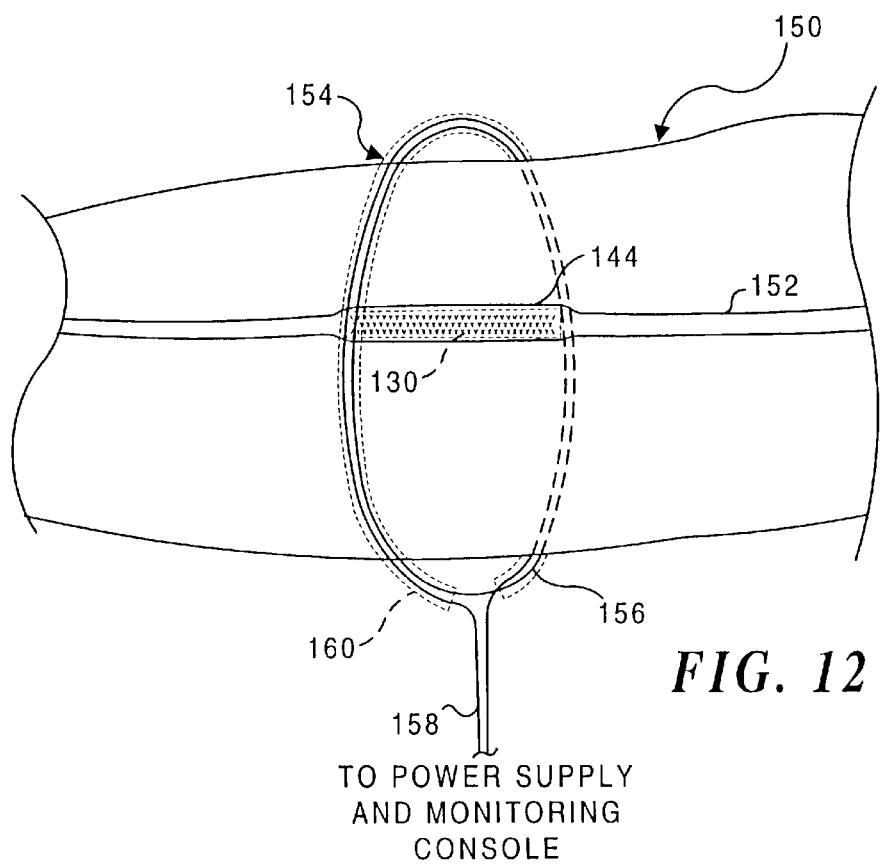
FIG. 12 is a cut-away view of a graft implanted at a substantial depth within a patient's body, showing an external coupling coil that encompasses the portion of the patient's body in which the graft is disposed.

In those cases where grafts are implanted relatively deep inside the patient's body, at some distance from the surface of the patient's skin, an alternative external coil 154 can be employed, generally as shown in FIG. 12. In this example, an artery 152 includes a graft 144 comprising RF coupling coil 130, which is disposed within a thigh 150 of the patient. To couple with RF coupling coil 130, RF coupling coil 154 includes a plurality of turns 156 sufficient in diameter to encompass thigh 150. An RF shield 160 encloses the outer extent of RF coupling coil 154, so that RF energy radiates only from the inner portion of coils 156. A lead 158 couples RF coupling coil 154 to the power supply and monitoring console (not shown in this Figure). RF coupling coil 154 can be made sufficiently large to encompass the portion of the body in which the implanted graft is disposed such as the torso, another limb of the patient, or the neck of the patient. Coupling is maximized between external coil 154 and coupling coil 130 (or other RF coupling coil) used on the graft when the central axes of both the RF coupling coil and the external antenna are coaxially aligned and when the implanted graft is generally near the center of the external coil. Coupling between the two coils decreases with increasing separation and begins to degrade when the implanted graft is more than one external coil radius away from the center point of the external coil. In addition, coupling is minimized when the central axes of the two coils are perpendicular.

Description of the Ultrasonic Transducer Arrays

An ultrasonic transducer for monitoring flow or fluid velocity through a graft should be relatively compact if it is to be mounted adjacent a natural graft or included in the wall of a synthetic graft. Typically, a prior art ultrasonic transducer includes an element comprising a planar slab of a piezoelectric material having conductive electrodes disposed on opposite sides thereof. Since such elements are relatively planar, they do not conform to the circular cross-sectional shape of a graft and therefore, are not compact or appropriate for use with a graft that is implanted within a patient's body and which is intended to be left in place for an extended period of time.

Figure 13:
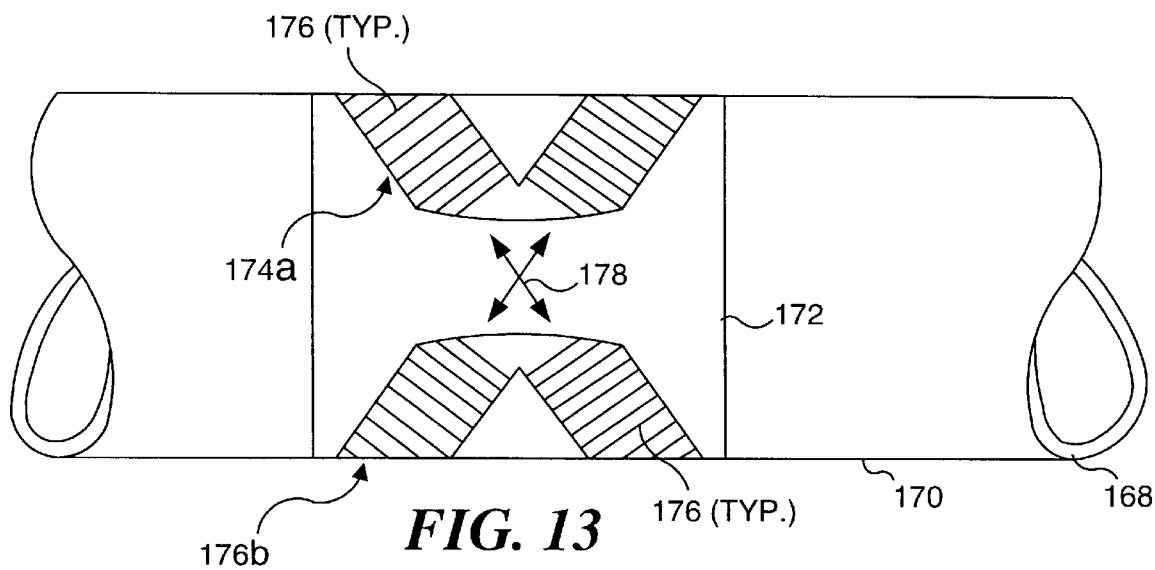
FIG. 13 is a side elevational schematic view of a dual beam conformal transducer array on a carrier band for use around a fluid carrying vessel, in accord with the present invention.

FIG. 13 shows an embodiment of an extremely low profile ultrasonic transducer comprising a conformal array 174a disposed on opposite sides of graft from a conformal array 174b. Ideally, the conformal array comprises a piezoelectric plastic used as a transduction material and having sufficient flexibility to allow the transducer elements to be wrapped around a wall 168 of a vessel 170. Such flexible piezoelectric plastic materials are readily available. It should be noted that vessel 170 may comprise either a natural or synthetic graft, or may instead be simply a part of the patient's vascular system. However, the compact, low profile aspect of the conformal transducer array makes it ideally suited for other applications outside the medical field. It is therefore contemplated that the conformal array ultrasonic transducer shown in FIGS. 13, 14, and 15 may alternatively be used in other commercial and industrial applications in which space around a vessel wall is at a premium and there is a need to monitor flow and/or velocity of a fluid through the vessel. Thus, the conformal array transducer may be used to monitor fluid flow or velocity through a plastic or metal pipe or tube. Furthermore, it can be used for either transit time or Doppler measurements. When used for transit time measurements, as shown in FIGS. 13 and 14, conformal arrays 174a and 174b are disposed generally on opposite sides of the vessel and encompass much of the circumference of the vessel.

However, when a pulsed Doppler measurement is made using the conformal array transducer, only a single such transducer is required, since it first produces an ultrasonic wave that is transmitted into the vessel and then receives an echo reflected back from the fluid flowing through the vessel. If used for continuous wave (CW) Doppler measurements, the pair of conformal array transducers disposed on opposite sides of the vessel are again needed, one transducer serving as a transmitter and the other as a receiver. In each case, it is presumed that the fluid has a non-zero velocity component directed along an ultrasonic beam axis of the ultrasonic wave produced by the conformal array transducer serving as a transmitter.

Figure 14:
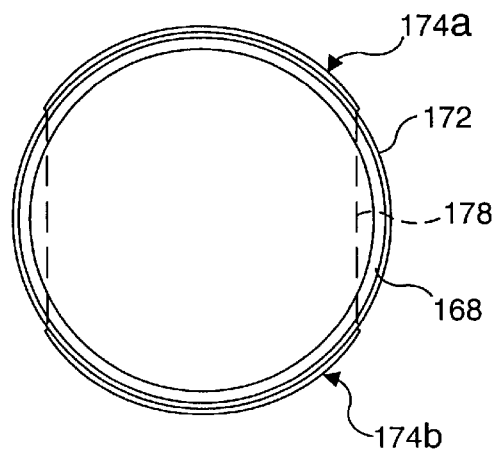
FIG. 14 is an end elevational view of the conformal transducer array of FIG. 13, around a vessel.
Figure 15:
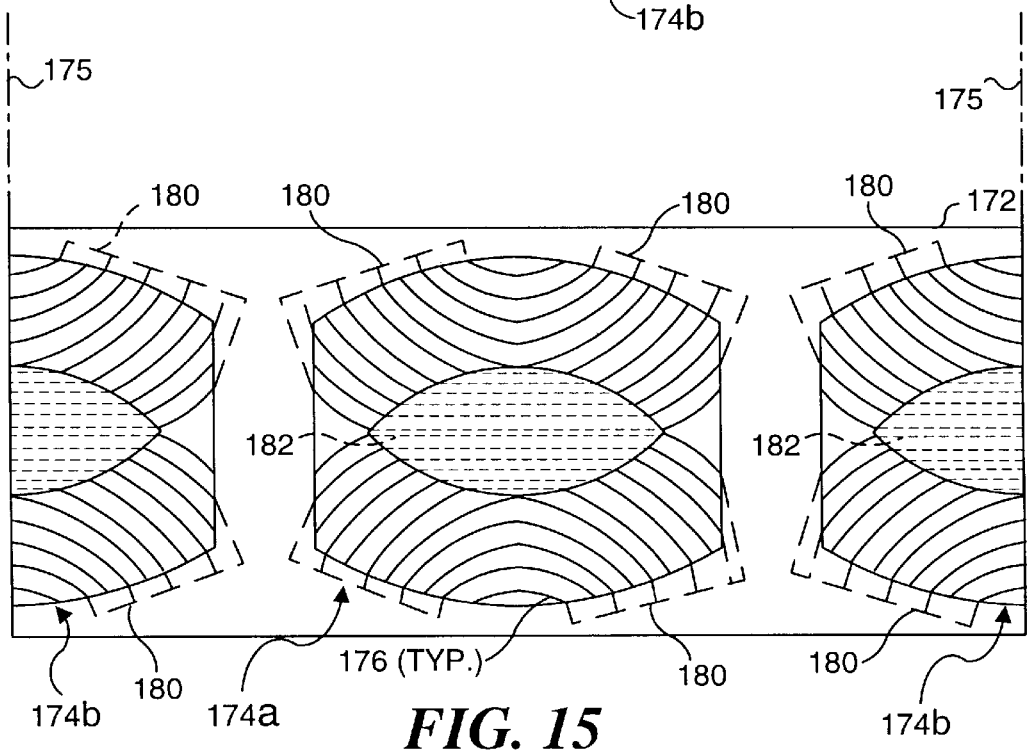
FIG. 15 is a plan view of the conformal transducer array shown in FIGS. 13 and 14, cut along a cut line to display the dual conformal arrays in a flat disposition.

Conformal arrays 174a and 174b shown in FIGS. 13–15 produce ultrasonic beams 178 that are tilted relative to the transverse direction across vessel 170 in substantially equal but opposite angles with respect to the longitudinal axis of the vessel. Since dual beam transit time measurements are implemented by conformal arrays 174a and 174b, the results are self-compensating for tilt angle errors. This form of self-compensation is only required where the alignment of the conformal array relative to the longitudinal axis of the vessel may be imperfect. For example, such imperfections are likely to occur when the conformal arrays are used in connection with monitoring the status of fluid flow through grafts or vascular vessels within a patient's body, since the grafts and vessels are not rigid and frequently are not straight—even within the limited length of the conformal array. For transit time measurements made on vessels wherein the alignment of the transducer relative to the longitudinal axis of the vessel is well known, an opposed pair of conformal arrays disposed on opposite sides of the vessel is sufficient so that the added complexity of the dual beam transducer geometry is not required for self compensation.

In the case of pulsed Doppler velocity measurements, a single transducer would again likely be adequate so long as the alignment of the transducer to the vessel is accurately controlled. If the alignment of the conformal array transducer is not controlled or not well known, a second such transducer can be used to gather velocity data along a second beam axis using pulsed Doppler velocity measurements. Assuming that the second axis is tilted in an equal but opposite direction as the first axis, the Doppler measurements made by the two conformal array transducers should be self-compensating for tilt errors. In this case, the second conformal array transducer could be mounted on the same or on an opposite side of the vessel from that where the first conformal array transducer is mounted to implement the Doppler measurements.

For CW or pseudo-CW Doppler velocity measurements (in which a relatively long duration pulse of ultrasonic waves is produced), the transit signal is applied for a sufficiently long period so that a second transducer is needed to receive the echo signals. In this case, a single set of diametrically opposed conformal array transducers can be used.

As perhaps best illustrated in FIG. 14, conformal array transducers 174a and 174b need not wrap entirely around vessel 170. In the illustrated embodiment, the conformal array transducers each span an arc of approximately 120° around the longitudinal axis of the vessel (i.e., about the center of the circular vessel as shown in FIG. 14). This geometry produces a measurement zone through which ultrasonic beams 178 propagate that is nominally equal to about 87% of the vessel outer diameter. Since vessel wall 168 has a finite thickness, the actual measurement zone (within the lumen of the vessel) exceeds approximately 90% of the vessel internal diameter. If used for Doppler velocity measurements, it is contemplated that the conformal array transducer need cover only a central portion of the vessel. As a result, the span of the conformal array transducer can be reduced from about 120° to something within the range from about 60° to about 90°.

To produce a wide, uniform ultrasound beam such as that needed for transit time measurements of flow, the conformal array transducer must produce ultrasonic waves having a wave front characterized by a substantially uniform amplitude and phase. As shown in FIG. 13, lateral projections through each of a plurality of transducer elements comprising the conformal array transducers are indicated by straight lines 176. These straight lines indicate the centers of the transducer elements and are perpendicular to the axis of propagation of waves 178 (represented by bidirectional arrows directed along the axes of propagation of the ultrasonic waves). In the preferred embodiment, the spacing between the element centers, i.e., between straight lines 176, is approximately equal to a phase angle of 90° at the transducer's excitation frequency. Thus, starting at the top of FIG. 13 and working downwardly, transducer elements disposed along each of the displayed straight lines produce acoustic waves that are successively delayed by 90°, or one-quarter wavelength in the fluid medium through which the ultrasonic waves propagate. For tissue, a sound velocity of 1,540 meters/second is normally assumed, so that the physical spacing of the projected straight lines would typically be defined by the following:

Projected Spacing in millimeters=$1.54/(4*F_0)$ where $F_0$ is equal to the center frequency in MHz. If zero degrees is assigned to the top-most element of conformal array 174a, the next element would operate at −90° relative to the top element, followed by an element operating at −180°, and then one operating at −270°, and finally by an element operating at 0° relative to the top electrode. Thus, conformal array 174a produces a succession of ultrasonic waves spaced apart by a 90° space shift, thereby achieving a desired phase uniformity across the transducer.

Amplitude uniformity can be achieved in the ultrasonic wave front by "shaving" the elements of the conformal array. Although shaving could be achieved in a variety of ways, the preferred embodiment controls shaving by varying the area of each element.

Conformal array transducers 174a and 174b are carried on a band 172 preferably made from the piezoelectric plastic material used for the element substrate, which is sized to fit snugly around an outer surface of vessel 170. Band 172 is intended to position the conformal array transducers in acoustic contact with vessel wall 168. Such contact assures that the ultrasonic waves produced by the element of the conformal array are conveyed through the vessel wall and into the fluid flowing through the interior of the vessel. Preferably, the piezoelectric plastic comprising band 172 is fabricated from a material such as polyvinylidene fluoride (PVDF), poly(vinyl cyanide-vinyl acetate) copolymer (P(VCN/VAc), or poly(vinylidene fluoride-trifluoroethylene) copolymer (P(VDF-TrFE)). Preferably, P(VDF-TrFE) is used because of its superior piezoelectric coupling and relatively lower losses.

Referring now to FIG. 15, further details of the conformal array transducers are illustrated. In this embodiment, alternating elements of the conformal array produce ultrasonic waves differing by 90°. In the view shown in FIG. 15, a cut line 175 intersects the lateral center of conformal array 174b. In practice, any cut would more likely extend through band 172 at a point approximately midway between conformal array 174a and conformal array 174b. If band 172 must be cut in order to wrap the band around a vessel 170, i.e., when it is not possible or practical to slip band 172 over the vessel uncut, the elements comprising the conformal array transducers need not be interrupted or damaged. Electrodes comprising each element of the conformal array can be photolithographically generated on the piezoelectric plastic substrate comprising band 172. Alternatively, the elements can be formed on a non-piezoelectric material comprising band 172, and then the material with the elements formed thereon can be bonded to a piezoelectric substrate in each area where a conformal array transducer element is disposed. In this latter embodiment, it is contemplated that a flex circuit material such as a polyimide could be employed for band 172, and that conventional photolithographic processing methods might be used to fabricate the conformal array transducer circuitry on the band. Further, the centers of alternating conformal array elements are coupled together electrically via conductors 180 (shown as dash lines) in FIG. 15. Not shown in FIGS. 13–15 are the leads that extend from an electronics assembly used to drive the conformal array. Any of the implantable electronic circuits shown in FIGS. 1–5 could be used for the electronics assembly.

The pattern of elements comprising each of the conformal array transducers and the boundary of each conformal array (top and bottom as shown in FIG. 15), define sinusoidal segments. The period of the sine wave from which these sinusoidal segments are derived is approximately equal to the circumference of band 172. Further, the amplitude of that sine wave generally depends on the desired beam angle relative to the longitudinal axis of vessel 170. For the sinusoidal segment employed for each electrode, the amplitude is defined by:

Amplitude=$D*\tan\Theta$

Similarly, the amplitude of the sinusoidal segment defining the boundary of each conformal array is defined by:

Amplitude=$D/(\tan\Theta)$ where $\Theta$ is equal to the angle between the longitudinal axis of the vessel and the ultrasound beam axis and D is equal to the external diameter of the vessel. Accordingly, it should be apparent that one sinusoidal template could be used to draw all of the transducer elements and a second sinusoidal template (differing only in amplitude from the first) could be used to draw the boundary of each conformal array transducer. The transducer elements are displaced or spaced apart from one another as required to achieve the phase relationship described above in connection with FIG. 13. In addition, the actual physical electrode pattern and placement of the elements on band 172 can be determined by finding intersection loci between band 172 as wrapped around vessel 170 and equally-spaced planes. The spacing between these planes is defined by the equation noted above for the projected spacing.

Conductors 180 that connect transducer elements of the same phase differ by 90°. There are two ways to achieve the 90° phase variation between the ultrasonic waves produced by successive electrodes in the conformal array. In the first approach, a uniformly polarized piezoelectric plastic substrate is used and every fourth element is connected together, producing four groups of elements or electrodes that produce ultrasonic waves having phasal relationships of 0°, 90°, 180°, and 270°, respectively. Alternatively, a zone polarized piezoelectric plastic substrate could be used and every other element can be connected together (as shown in FIG. 15). Each of these two groups is then connected to provide an in phase and a quadrature phase transceiving system, so that ultrasonic waves are produced by the elements having a relative phase relationship of 0° and 90°. In the first approach, a multi-layer interconnect pattern is required to connect to all traces for each of the transducer elements in the four groups. In addition, a more complex four-phase electronic driving system that includes a phase shifter is required. Specifically, the signal applied to each of the four groups must differ by 90° between successive elements to achieve the 0°, 90°, 180°, and 270° driving signals. The phase shifter, e.g., included in the modulator that drives the transducer, provides the phase shifted excitation signals applied to each successive element of the transducer.

In the second approach, which is preferred because it simplifies the electronic package required and because it facilitates use of a simpler, double-sided electrode pattern, the piezoelectric plastic material must be locally polarized in a specific direction, depending upon the desired phase of the electrode at that location. A polarity reversal provides a 180° phase shift, eliminating the need for 180° and 270° electronic signals. Thus, the zones of the substrate designated as 0 and 90° would be connected to the signal source with the poles of the elements in one direction, while zones for elements designated to provide a relative phase shift of 180° and 270° would be connected with the poles of the elements in the opposite direction. Elements producing ultrasonic waves with a relative phase relationship of 0° and 180° would comprise one group, and elements producing ultrasonic waves with a relative phase relationship of 90° and 270° would comprise a second group. Connecting the poles of the different groups in local regions in opposite directions is achieved by applying electric fields of opposite polarity in those areas during manufacture of the conformal array transducer. The final element wiring pattern required to actually energize the conformal array transducer when it is employed for monitoring flow and/or velocity of fluid through the vessel would preclude applying electric fields in opposite polarity. Accordingly, the required poling relationship would have to be performed using either temporary electrodes or by providing temporary breaks in the actual electrode pattern employed in the final conformal array transducer.

In the preferred embodiment, to achieve a desired frequency of operation, it is contemplated that the electrode mass would be increased to a point well beyond that required for making electrical connections. This added mass would act together with the piezoelectric plastic material to form a physically resonant system at a desired frequency. In this manner, a relatively thinner and more flexible piezoelectric plastic material can be used for the substrate comprising band 172. Use of mass loading in this manner is well known to those of ordinary skill in the art of transducer design, at least in connection with producing large, single element, piston transducers.

Figure 16:
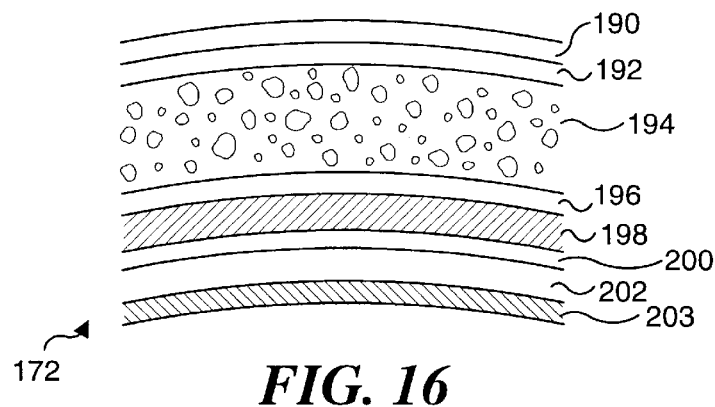
FIG. 16 is an enlarged partial transverse cross-sectional view of the layers comprising the conformal transducer array mounted on a carrier band that is disposed around a vessel wall.

The conformal array transducers can be formed on band 172, but alternatively, can be included within the structure of a synthetic graft. FIG. 16 illustrates a portion of a cross-sectional view of the conformal array transducer fabricated on band 172. The entire transducer assembly is covered with an outer coating 190 made from a biocompatible material that serves as a barrier to protect the conformal array transducer from bodily fluids. Below the outer coating is an RF shield 192, comprising electrically conductive flexible material or a thin foil that provides RF shielding to minimize EMI radiated from the conformal array transducer assembly. An acoustic backing 194 comprising a conventional, or a syntactic foam, i.e., a polymer loaded with hollow microspheres, such as is well known to those of ordinary skill in the art, serves both for acoustic isolation and dampening and to minimize capacitive loading. The acoustic backing has a relatively low dielectric constant, thereby minimizing capacitive loading between the electrodes and surrounding tissue. Acoustic backing 194 thus insulates the transducer elements from the surrounding fluid and tissue in a capacitive sense, and also in an acoustic sense. The next layer radially closer to the longitudinal center of the vessel comprises a rear electrode 196. A front electrode 200 is spaced apart from the rear electrode by a piezoelectric plastic layer 198. As noted above, in the preferred embodiment illustrated in FIGS. 13–15, piezoelectric plastic layer 198 comprises band 172. Piezoelectric layer 198 (or band 172) has a relatively low dielectric constant, e.g., from about six to eight) compared to tissue (approximately 80).

Rear electrode 196 and front electrode 200 preferably comprise multi-layer structures (although separate layers are not shown). For example, the electrodes will include a metallic layer that bonds well to the piezoelectric plastic material, for example, titanium, followed by a highly conductive layer, for example, copper, followed by an oxidation resistant layer, for example, gold. Such multi-layer systems are well known in the field of electronic interconnects and are ideally suited for use as electrodes in the conformal array transducer. Preferably, front electrode 200 is the "common electrode" for the transducer elements and serves as an RF shield. A front coating 202 serves as an acoustic coupling between the conformal array transducer and the vessel about which it is applied. In addition, the front coating layer serves as a biocompatible layer, providing a barrier to fluid ingress into the conformal array transducer. The transducer assembly comprising each of the layers disclosed above is wrapped around and in contact with a vessel wall 203 as shown in FIG. 16.

Figure 17:
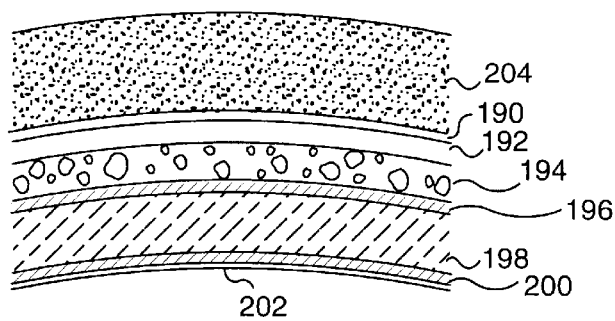
FIG. 17 is an enlarged partial transverse cross-sectional view of the layers comprising the conformal transducer array disposed within a vessel wall of a synthetic graft.

Referring now to FIG. 17, an embodiment of the conformal transducer array fabricated as an integral component of a wall of a synthetic graft is illustrated (only a portion of a cross section showing the plurality of layers comprising the device is illustrated). A synthetic graft material 204 provides the primary structure for the synthetic graft and is adapted to be installed in a patient's vascular system. Typically, the graft material will comprise either a foamed fluoropolymer such as that sold by Gortex Corporation, or a fabric such as DACRON. The graft material is characterized by a moderate attenuation of ultrasonic signals and a structure that is somewhat porous to bodily fluids. Below graft material 204 is disposed outer coating 190 comprising a biocompatible material that protects the transducer elements, and other components of the transducer system from bodily fluids that may permeate the graft material. Below outer coating 190 is disposed RF shield 192, to minimize transmission of EMI outside the patient's body. Acoustic backing 194 is disposed between RF shield 192 and rear electrode 196, and as described above, is a relatively lossy material. Piezoelectric material 198 couples rear electrode 196 and front electrode 200 and comprises one of the flexible piezoelectric plastics noted above. Front coating 202 is applied to the inner surface of the graft and transducer assembly and is selected for its biocompatibility, to withstand exposure to the bodily fluids flowing through the graft.

In both the conformal array transducer assembly provided in band 172 (as shown in FIGS. 13–15) and the transducer assembly included within the structure of the synthetic graft wall, as illustrated in FIG. 17, it is contemplated that adhesive layers (not shown) may be used between the various layers. However, certain layers such as front and rear electrodes 200 and 196 will likely need not be adhesively coupled to the piezoelectric material if photolithographically formed on the material. Other layers may not require an adhesive to couple to adjacent layers, e.g., if formed of a thermoset material that self bonds to an adjacent layer when set.

Figure 18:
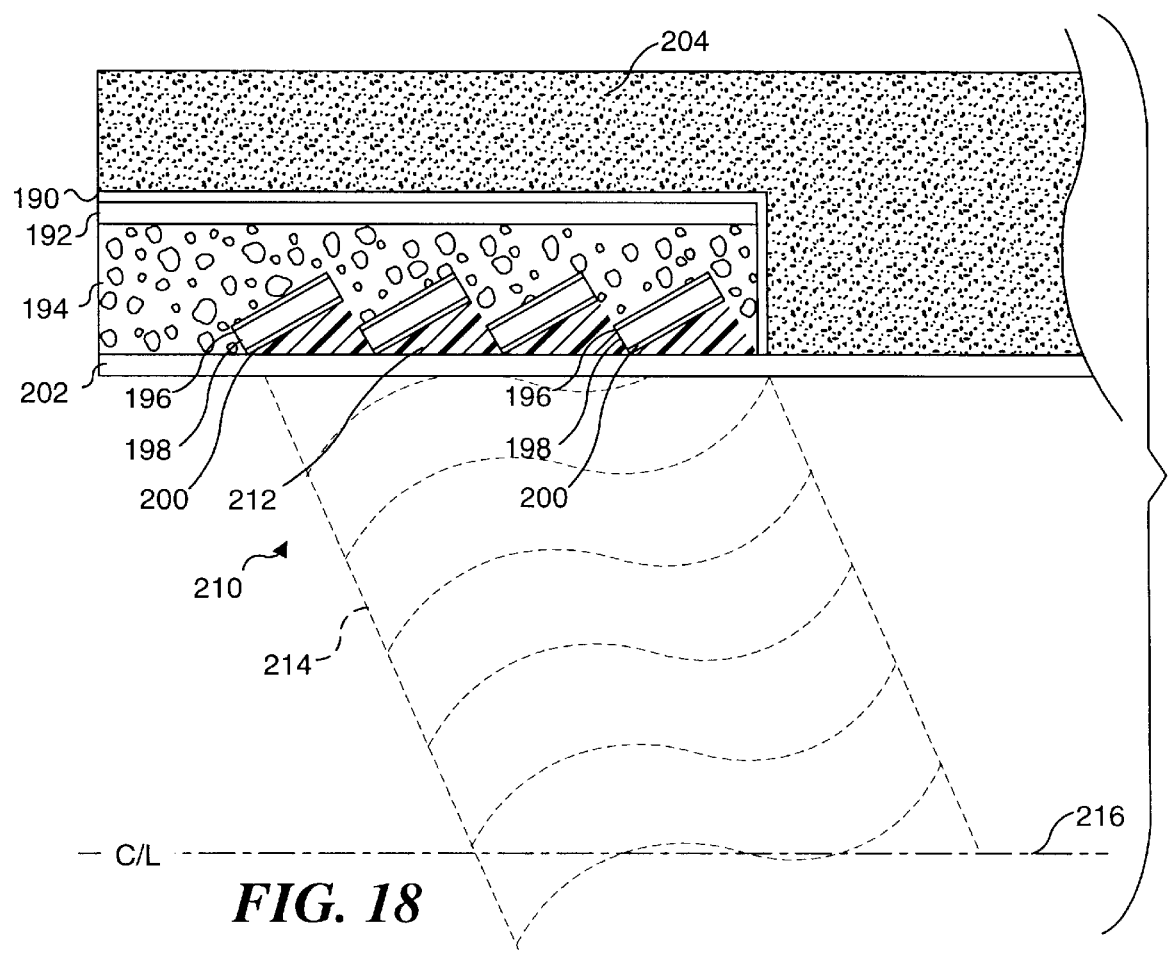
FIG. 18 is an enlarged partial cross-sectional side view of a tilted element transducer array disposed within a wall of a synthetic graft.

As noted above, one of the advantages of the conformal array transducer is its relatively low profile. In some cases, a synthetic graft may accommodate a relatively thicker profile transducer assembly within its wall. An embodiment of a tilted element transducer 210 is illustrated in FIG. 18. Each element comprising tilted element transducer 210 includes rear electrode 196 and front electrode 200 disposed on opposite sides of piezoelectric material 198. Conventional prior art transducers for producing an ultrasonic waves use a single such element that has a substantially greater width that is too great for inclusion in the wall of a graft. In contrast, tilted element transducer 210 includes a plurality of elements like those shown in FIG. 18 that minimize the radial height (or thickness) of the transducer.

The tilted element transducer is built into the wall of the synthetic graft, generally as shown in FIG. 18 and includes coating 190, which again serves the function of providing a biocompatible layer to protect the interior portion of the graft and the transducer components contained therein from exposure to bodily fluids outside the graft. Inside outer coating 190 is synthetic graft material 204, which comprises the overall structure of the graft. RF shield 192 extends over the portion of the graft in which tilted element transducer array 210 is disposed within the protection provided by coating 190. Below RF shield 192 is disposed acoustic backing 194.

An acoustic filler material 212 is disposed between front electrode 198 and front coating 202, on the interior surface of the synthetic graft, and is used to fill in the cavities in front of the transducer elements. The acoustic filler material is characterized by a relatively low ultrasonic attenuation, so that it readily conveys the ultrasonic waves produced by the elements into the lumen of the graft. In order to minimize reverberations of the ultrasonic waves in this acoustic filler material, its acoustic impedance, which is equal to sound velocity times density, is approximately equal to that of the fluid in the vessel. The velocity of sound in the acoustic filler material should also be close to that of the fluid flowing through the graft so that the sound beam is not significantly deflected by the acoustic filler material. Alternatively, an acoustic filler material having a relatively low sound velocity compared to the fluid may be used. In this case, the acoustic filler material acts as an acoustic lens that deflects the sound being produced by the tilted transducer elements, for example, materials such as silicones or fluorosilicones, typically having sound velocities about 1000 meters per second (compared to a sound velocity of approximately 1540 meters per second for blood), may be used. Low velocity lenses are generally well known in the art of ultrasonic transducers. The benefit of using a low velocity acoustic filler material is that the tilted transducer elements can be tilted about 30% less than would be required otherwise. As a result, the overall height of the tilted element transducer portion of the synthetic graft can be made about 30% thinner than would be possible without the low velocity acoustic filler material. In combination, the plurality of tilted elements produce an ultrasonic wave 214 that propagates at an angle relative to the longitudinal axis of the synthetic graft, which is represented by a center line 216 in FIG. 18.

Figure 19A:
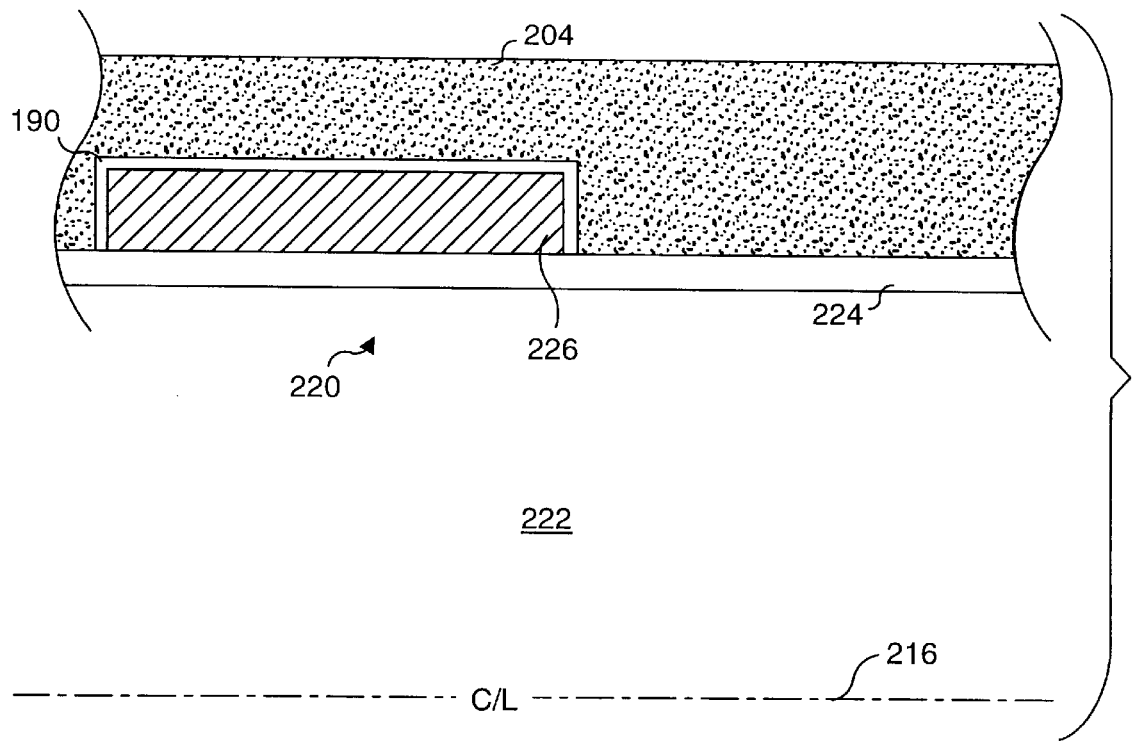
FIG. 19A is an enlarged partial cross-sectional side view of a pressure transducer disposed within the wall of a synthetic graft.
Figure 19B:
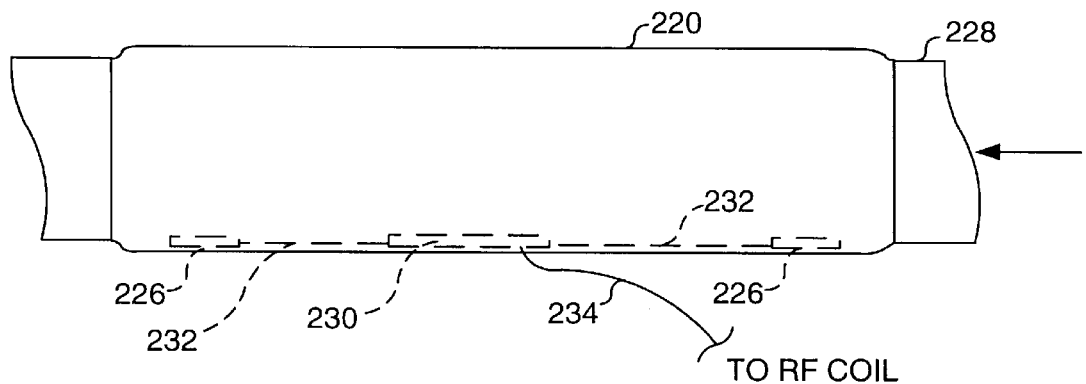
FIG. 19B is an enlarged side elevational view of a graft in which are disposed a pair of pressure transducers.

In FIGS. 19A and 19B, an artificial graft 220 is illustrated in which pressure transducers 226 are incorporated within the wall of the graft for monitoring the pressure of fluid passing through the graft. Layer 190 of the biocompatible material is disposed between graft material 204 and transducers 226 and is employed to protect the transducers, and other components of the transducer system from bodily fluids that may permeate the graft material. As shown in FIG. 19B, two pressure transducers 226 are employed, one being used for monitoring the proximal fluid pressure and the other for monitoring the distal fluid pressure. To accommodate measurements of proximal and distal fluid pressure, pressure transducers 226 are disposed adjacent the entrance and exit ends of artificial graft 220, respectively.

Pressure transducer 226 may comprise one of several different types of devices for sensing pressure. Such devices include an integrated circuit pressure sensor, a strain-type pressure sensor, such as a resistive strain gauge that responds to fluid pressure, etc. Various types of pressure sensing devices appropriate for incorporation in the wall of a graft are readily available from a number of different commercial sources. Pressure transducers 226 are coupled through leads 232 to an implantable electronic circuit 230, such as that illustrated in FIG. 6, as discussed above. A line 234 connects the circuit to a remotely disposed RF coupling coil (not shown in FIG. 19B) like one of those discussed above in connection with FIGS. 7 and 8, or to one disposed within the wall of the graft, as also discussed above. The interior surface of synthetic graft 220 includes an internal coating 224 that conveys pressure readily from the fluid flowing through an interior 222 of the artificial graft to pressure transducers 226. Inner coating 224 is biocompatible and comprises an elastomeric material.

Figure 20A:
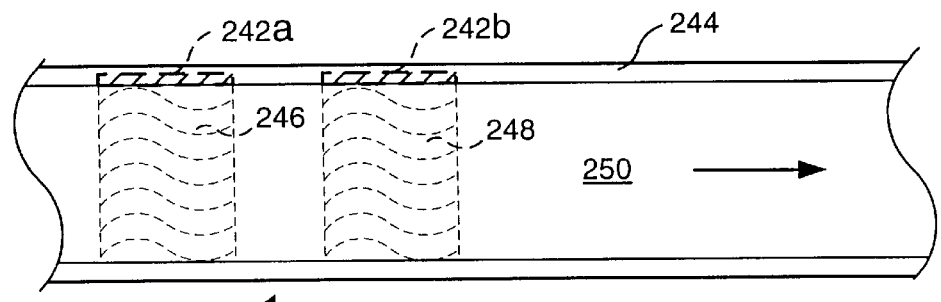
FIG. 20A is a cross-sectional side view of a portion of a synthetic graft in which are disposed transversely oriented transducers for monitoring flow using correlation measurements.
Figure 20B:
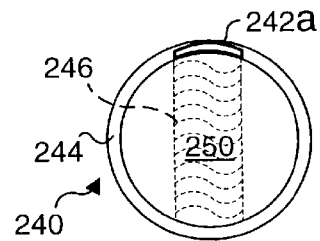
FIG. 20B is a transverse cross-sectional view of the synthetic graft shown in FIG. 20A.

In FIGS. 20A and 20B, an alternative approach for monitoring the velocity of a fluid through an interior 250 of a graft 240 is illustrated. In this embodiment, a pair of ultrasonic transducers 242a and 242b are mounted in relatively close proximity within the wall 244 of synthetic graft 240. Alternatively, the ultrasonic transducers may be disposed externally in contact with the outer surface of a natural graft (not shown). Ultrasonic transducers 242a and 242b each produce a pulse and receive the echo back from fluid flowing through interior 250 of the graft, the echoes being scattered from the fluid flowing therein. In this embodiment, the signals 246 received from transducer 242a in response to the echo is correlated with the similar signal 248 from ultrasonic transducer 242b, resulting in a time delay estimate. The velocity of the fluid is then computed by dividing a distance between the center of transducer 242a and the center of transducer 242b by the time delay that was determined from the correlation analysis.

Unlike a Doppler system, the echoes in a correlation type transducer system like that shown in FIGS. 20A and 20B are not frequency shifted. Instead, the velocity signal is extracted by correlating the echo amplitude versus time signals for a pair of range bins. The velocity versus time is independently determined for each range bin, resulting in a time dependent velocity profile across the diameter of the vessel or graft.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A system for monitoring a parameter indicative of a condition of a vessel relating to its ability to convey a fluid, said system comprising:
   (a) a carrier band that is adapted to couple about the vessel so that the carrier band is in close proximity to at least one side of the vessel;
   (b) a first transducer having a plurality of conformal elements disposed in a spaced-apart array on the carrier band, said plurality of conformal elements being sufficiently flexible and shaped so that they are adapted to curve about the vessel, conforming to its shape, said first transducer being adapted to couple to a telemetry radio frequency signal and producing ultrasonic waves when excited by the telemetry radio frequency signal that are emitted from the plurality of conformal elements and are directed into an interior of the vessel; and (c) a receiver disposed to receive the ultrasonic waves after they have propagated at least partially through the vessel, said receiver producing a signal indicative of an effect on the ultrasonic waves due to the fluid in the vessel and thus, indicative of a parameter relating to a flow of the fluid through the vessel.

2. The system of claim 1, wherein ultrasonic waves are emitted as a pulse, the first transducer alternately comprising an emitter of the pulse of the ultrasonic waves, and then comprising the receiver, said pulse of ultrasonic waves being reflected from the fluid in the vessel back toward the first transducer.

3. The system of claim 1, wherein the vessel comprises a graft adapted to be disposed within a patient's body, said system being used to monitor the flow of the fluid through the graft to determine whether the flow of the fluid through the graft is being blocked.

4. The system of claim 3, further comprising a coil adapted to receive power from an external source and to provide an electrical current that is used for energizing components of the system.

5. The system of claim 4, wherein the coil is disposed within a wall of the graft.

6. The system of claim 4, wherein the coil is disposed on the carrier band.

7. The system of claim 4, further comprising a power supply, and a multiplexer, both being adapted to be internally disposed within the patient's body, said multiplexer alternately coupling the coil to the receiver and then to the power supply, so that power from the external source is supplied to the power supply when the coil is coupled to the power supplied by the multiplexer, and the signal produced by the receiver is supplied to the coil when the coil is coupled to the receiver.

8. The system of claim 1, further comprising a second transducer having a plurality of conformal elements disposed in a spaced-apart array on the carrier band, said plurality of conformal elements being sufficiently flexible and shaped so that they are adapted to curve about the vessel, conforming to its shape, said first transducer being and are directed into an interior of the vessel.

9. The system of claim 8, wherein the carrier band comprises a substrate of a piezoelectric material on which a plurality of electrodes are formed to define the conformal elements of the first and the second transducers.

10. The system of claim 9, wherein the piezoelectric material is uniformly polarized, every fourth electrode of the plurality of electrodes being coupled together.

11. The system of claim 9, wherein the piezoelectric material is zone polarized, every other electrode comprising the plurality of electrodes being coupled together.

12. The system of claim 9, wherein the carrier band further comprises an acoustic backing layer encompassing the plurality of electrodes that are formed on the piezoelectric material.

13. The system of claim 9, wherein the carrier band further comprises a radio frequency shield encompassing the plurality of electrodes formed on the piezoelectric material.

14. The system of claim 1, wherein the ultrasonic waves emitted by successive elements of the first transducer are 90° out of phase, so that the ultrasonic waves emitted in one direction are canceled due to a destructive interference.

15. The system of claim 8, wherein said second transducer is adapted to couple to the radio frequency signal and produces ultrasonic waves when excited by the radio frequency signal, said first transducer and said second transducer alternately interchangeably functioning as the receiver and as an emitter of the ultrasonic waves during successive time intervals.

16. The system of claim 8, wherein the first transducer and the second transducer are disposed on opposite sides of the carrier band when it is fitted about the vessel, said second transducer comprising the receiver of the ultrasonic waves emitted by the first transducer, said parameter being determined as a function of a transit time for the ultrasonic waves to pass through the vessel.

17. The system of claim 8, wherein the conformal elements of the first transducer and of the second transducer are shaped like segments of a sine wave having a period substantially equal to a circumference of the vessel.

18. The system of claim 17, wherein an amplitude of the sine wave having segments relating to the shape of the conformal elements substantially determines a beam angle of the ultrasonic waves.

* * * * *